United States Patent [19]

Doak et al.

[11] Patent Number: 5,662,633
[45] Date of Patent: Sep. 2, 1997

[54] ABSORBENT ARTICLE HAVING A WINDOW WITH A BODY-CONFORMING ACQUISITION ELEMENT POSITIONED THEREIN

[75] Inventors: Nancy Beck Doak, Cincinnati, Ohio; Theresa Louise Johnson, New Castle, Del.; Hugh Ansley Thompson, Fairfield; Robb Eric Olsen, Cincinnati, both of Ohio

[73] Assignee: The Procter & Gamble Company, Cincinnati, Ohio

[21] Appl. No.: 444,079

[22] Filed: May 17, 1995

Related U.S. Application Data

[63] Continuation of Ser. No. 84,048, Jun. 28, 1993, abandoned, which is a continuation-in-part of Ser. No. 734,404, Jul. 23, 1991, abandoned, Ser. No. 734,405, Jul. 23, 1991, Pat. No. 5,334,176, Ser. No. 915,134, Jul. 23, 1992, abandoned, Ser. No. 915,201, Jul. 23, 1992, abandoned, Ser. No. 915,202, Jul. 23, 1992, abandoned, Ser. No. 915,285, Jul. 23, 1992, abandoned, Ser. No. 915,286, Jul. 23, 1992, Pat. No. 5,382,245, and Ser. No. 934,585, Aug. 24, 1992, Pat. No. 5,281,208, which is a continuation of Ser. No. 734,392, Jul. 23, 1991, abandoned.

[51] Int. Cl.$^6$ .............................. A61F 13/15; A61F 13/20
[52] U.S. Cl. .................................................. 604/378
[58] Field of Search .............................. 604/358, 368, 604/369, 372, 378–380, 385.1

[56] References Cited

U.S. PATENT DOCUMENTS

| | | | |
|---|---|---|---|
| Re. 24,137 | 4/1956 | Jacks | 604/378 |
| 1,997,883 | 4/1935 | Lesselbaum et al. | |
| 2,331,355 | 10/1943 | Strongson | 604/385.1 |
| 3,559,648 | 2/1971 | Mason, Jr. | 604/378 |
| 3,779,246 | 12/1973 | Mesek et al. | 604/378 |
| 4,029,100 | 6/1977 | Karami | |
| 4,079,739 | 3/1978 | Whitehead | |
| 4,333,463 | 6/1982 | Holtman | |
| 4,338,371 | 7/1982 | Dawn et al. | 604/368 |
| 4,433,972 | 2/1984 | Malfitano | |
| 4,501,587 | 2/1985 | Enloe | 604/385.1 |
| 4,631,062 | 12/1986 | Lassen et al. | |
| 4,676,786 | 6/1987 | Nishino | 604/384 |
| 4,743,245 | 5/1988 | Lassen et al. | |
| 4,828,555 | 5/1989 | Hermansson | 604/379 |
| 4,846,824 | 7/1989 | Lassen et al. | |
| 4,988,344 | 1/1991 | Resising et al. | |
| 4,988,345 | 1/1991 | Reising | |
| 5,012,540 | 5/1991 | Hockaday | |
| 5,171,302 | 12/1992 | Buell | |
| 5,181,563 | 1/1993 | Amaral | |

(List continued on next page.)

FOREIGN PATENT DOCUMENTS

| | | |
|---|---|---|
| WO93/09744 | 5/1993 | European Pat. Off. |
| WO93/11727 | 6/1993 | European Pat. Off. |
| WO93/01781 | 2/1993 | WIPO |
| WO93/01782 | 2/1993 | WIPO |
| WO93/01783 | 2/1993 | WIPO |
| WO93/01784 | 2/1993 | WIPO |
| WO93/01785 | 2/1993 | WIPO |
| WO93/01786 | 2/1993 | WIPO |
| WO93/02251 | 2/1993 | WIPO |
| 93001779 | 2/1993 | WIPO ........................ 604/378 |

*Primary Examiner*—P. Zuttarelli
*Attorney, Agent, or Firm*—Edward J. Milbrada; Jeffrey V. Bamber; Steven W. Miller

[57] ABSTRACT

An absorbent article, such as a sanitary napkin is provided. The sanitary napkin of the present invention has at least one component facing the body surface of the sanitary napkin having a window cut out therein. The sanitary napkin is provided with an acquisition/distribution component such as a tow of resilient fibers having intra-fiber capillary channels. The tow of resilient fibers is positioned so that it at least partially lies in the space defined by the window. The acquisition/distribution component has a compressed configuration and an uncompressed configuration. In its uncompressed configuration, the acquisition/distribution component lies relatively flat behind the window. In its compressed configuration, the acquisition/distribution component forms a hump on the body surface that protrudes from the window.

33 Claims, 4 Drawing Sheets

U.S. PATENT DOCUMENTS

| | | |
|---|---|---|
| 5,197,959 | 3/1993 | Buell . |
| 5,219,341 | 6/1993 | Serbiak . |
| 5,267,952 | 12/1993 | Gardner . |
| 5,281,208 | 1/1994 | Thompson et al. . |
| 5,334,176 | 8/1994 | Buenger et al. . |
| 5,382,245 | 1/1995 | Thompson et al. ............... 604/368 |
| 5,429,629 | 7/1995 | Latimer et al. ............... 604/358 |
| 5,533,991 | 7/1996 | Kirby et al. . |

ABSORBENT ARTICLE HAVING A WINDOW WITH A BODY-CONFORMING ACQUISITION ELEMENT POSITIONED THEREIN

This application is a continuation of application Ser. No. 08/084,048, filed Jun. 28, 1993 now abandoned, which was a continuation-in-part application of the following U.S. Pat. Applications:

application Ser. No. 07/934,585 filed Aug. 24, 1992 now U.S. Pat. No. 5,281,208 which was a continuation of application Ser. No. 07/734,392 filed Jul. 23, 1991, now abandoned; application Ser. No. 07/915,134 filed Jul. 23, 1992, now abandoned, application Ser. No. 07/734,404 filed Jul. 23, 1991, now abandoned, application Ser. No. 07/734,405 filed Jul. 23, 1991, now U.S. Pat. No. 5,334,176, application Ser. No. 07/915,201 filed Jul. 23, 1992, now abandoned, application Ser. No. 07/915,202 filed Jul. 23, 1992, now abandoned, application Ser. No. 07/915,285 filed Jul. 23, 1992, now abandoned, and application Ser. No. 07/915,286 filed Jul. 23, 1992, now U.S. Pat. No. 5,382,245.

FIELD OF THE INVENTION

The present invention relates to absorbent articles, especially catamenial articles such as sanitary napkins. More particularly, this invention is directed to a sanitary napkin having a window with a body-conforming acquisition element positioned therein.

BACKGROUND OF THE INVENTION

A wide variety of types of structures for disposable absorbent articles used to collect body fluids are known in the art. Commercial absorbent articles include diapers, adult incontinence products, catamenials and bandages. Disposable products of this type comprise components for receiving, absorbing and retaining fluids. Typically, such articles include a liquid permeable topsheet, an absorbent core and a liquid impermeable backsheet.

Improving the performance of absorbent articles such as sanitary napkins continues to be a formidable undertaking, although a number of improvements have been made in both their materials and structures. A number of efforts have been directed to providing sanitary napkins with the ability to remain in contact with the wearer's body and to acquire bodily exudates immediately upon leaving the body and then to distribute the exudates throughout the absorbent core of the napkin.

Examples of such sanitary napkins are disclosed in PCT International Publication Nos.: WO 93/01779 and WO 93/02251 which disclose sanitary napkins employing fibers having intra-fiber capillary channels (which may be referred to herein as the "Capillary Channel Fiber" patent applications); and in the following pending U.S. Patent Applications which were filed on Jul. 23, 1992: U.S. patent application Ser. No. 07/915,202, entitled "Curved, Shaped Absorbent Article" filed in the name of Theresa L. Johnson, et al. (PCT Publication No. WO 93/01781); U.S. patent application Ser. No. 07/915,285, entitled "Absorbent Article Having Resilient Center" filed in the name of Thomas W. Osborn, et al. (PCT Publication No. WO 93/01782); U.S. patent application Ser. No. 07/915,201, entitled "Absorbent Article Fastener Pattern" filed in the name of Robb E. Olsen, et al. (PCT Publication No. WO 93/01783); and, U.S. patent application Ser. No. 07/915,134, entitled "Method of Making Curved, Shaped Absorbent Article" filed in the name of Letha M. Hines, et al. (PCT Publication No. WO 93/01784) which disclose the use of capillary channel fibers that may be arranged in the form of a tufted bundle (or "bun") on a curved, body-shaped absorbent article (and, as a result may be referred to herein as the "Curved Bun" patent applications); and in WO 93/01785 and WO 93/01786 which disclose extensible and stretchable sanitary napkins; all of which are incorporated by reference herein.

In one preferred embodiment described in the "Capillary Channel Fiber" and "Curved Bun" patent applications, the capillary channel fibers are formed into a tufted bundle that is pulled through a confining slit in a sheet of material. The sheet of material having the confining slit retains the bun in its tufted configuration. The bun provides a rounded or curved surface for placement adjacent the space between the wearer's labia.

The sanitary napkins described in these patent publications work quite well. There are, however, some aspects of the sanitary napkins that are described in these publications that can be improved. For example, it is desirable to provide a sanitary napkin with an alternative structure to a tufted bundle that is pulled through a confining slit in a sheet of material due to the complexities of carrying out such an operation during manufacture of the sanitary napkin. Therefore, the search for improved, as well as alternative, sanitary napkins (particularly to those described in the "Capillary Channel Fiber" and "Curved Bun" patent applications) has continued.

A need exists for a sanitary napkin that is at least as unobtrusive and comfortable to wear as those described in the "Capillary Channel Fiber" and "Curved Bun" patent publications incorporated by reference above. In addition, a need exists for a sanitary napkin that is at least as easy to construct, or preferably even easier to construct, as those sanitary napkins described in the above "Capillary Channel Fiber" and "Curved Bun" patent publications.

It is, therefore, an object of the present invention to provide disposable absorbent articles having the ability to acquire bodily exudates immediately upon leaving the body and then to distribute the exudates throughout the absorbent core of the article.

It is another object of the present invention to provide absorbent articles that are at least as unobtrusive and comfortable to wear as those described in the "Capillary Channel Fiber" and "Curved Bun" patent publications incorporated by reference above.

It is another object of the present invention to provide absorbent articles having the above characteristics which are easily and inexpensively manufactured.

These and other objects of the present invention will be more readily apparent when considered in reference to the following description and when taken in conjunction with the accompanying drawings.

SUMMARY OF THE INVENTION

The present invention provides an absorbent article, such as a sanitary napkin having a component with a window that has a body-conforming acquisition element positioned therein.

The sanitary napkin has a body side, a garment side, a longitudinal centerline, and a transverse centerline. The sanitary napkin comprises a liquid pervious topsheet, a liquid impervious backsheet joined to the topsheet, and an absorbent core and a body-conforming acquisition element positioned between the topsheet and backsheet. The sanitary napkin preferably also has a wicking layer or secondary topsheet positioned between the topsheet and absorbent core. The sanitary napkin further comprises a fastener for attaching the sanitary napkin to the crotch region of the wearer's panties.

In a preferred embodiment, the core comprises an upper portion facing the topsheet, a lower portion facing the backsheet, and an intermediate portion positioned between the upper and lower portions. The upper portion of the core and the wicking layer both have a window forming an opening therein. An acquisition/distribution component is positioned so that it at least partially lies in the opening defined by the window. In a particularly preferred embodiment, the absorbent core comprises a laminate of superabsorbent material positioned between two layers or webs of modified cross-linked cellulosic fibers. The acquisition/distribution component preferably comprises a wet and dry resilient material. One suitable resilient material comprises a bundle of longitudinally-oriented capillary channel fibers (i.e., fibers having intra-fiber capillary channels, especially on their exterior surfaces) arranged in the form of a staple sliver of fibers (i.e., a structure comprised of loosely gathered or entangled fibers of a particular length). The acquisition/distribution component (such as the sliver of capillary channel fibers) is preferably positioned between the layers of cross-linked cellulosic fibers comprising the absorbent core so that a portion of it lies within the window provided in the upper portion of the core.

The portion of the acquisition/distribution component (the sliver of capillary channel fibers) within the window has a compressed configuration when it is subjected to laterally inward compressive forces by the insides of the wearer's thighs. When it is in its compressed configuration, the acquisition/distribution component forms a hump on the body surface of the sanitary napkin that protrudes from the window and conforms to the wearer's body. The acquisition/distribution component has an uncompressed configuration when the compressive forces supplied by the wearer's thighs are absent. When the acquisition/distribution component is in its uncompressed configuration, it lies relatively flat inside and under the window.

DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

DETAILED DESCRIPTION OF THE INVENTION

1. General Characteristics of the Absorbent Article.

A preferred embodiment of the disposable absorbent article of the present invention is the sanitary napkin 20, shown in FIGS. 1–4.

The term "absorbent article", as used herein, refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner).

The term "sanitary napkin", as used herein, refers to an absorbent article which is worn by females adjacent to the pudendal region, generally external to the urogenital region, and which is intended to absorb and contain menstrual fluids and other vaginal discharges from the wearer's body (e.g., blood, menses, and urine). It should be understood, however, that the present invention is also applicable to other feminine hygiene or catamenial pads such as pantiliners, or other absorbent articles such as incontinence pads, and the like.

Figure 1:
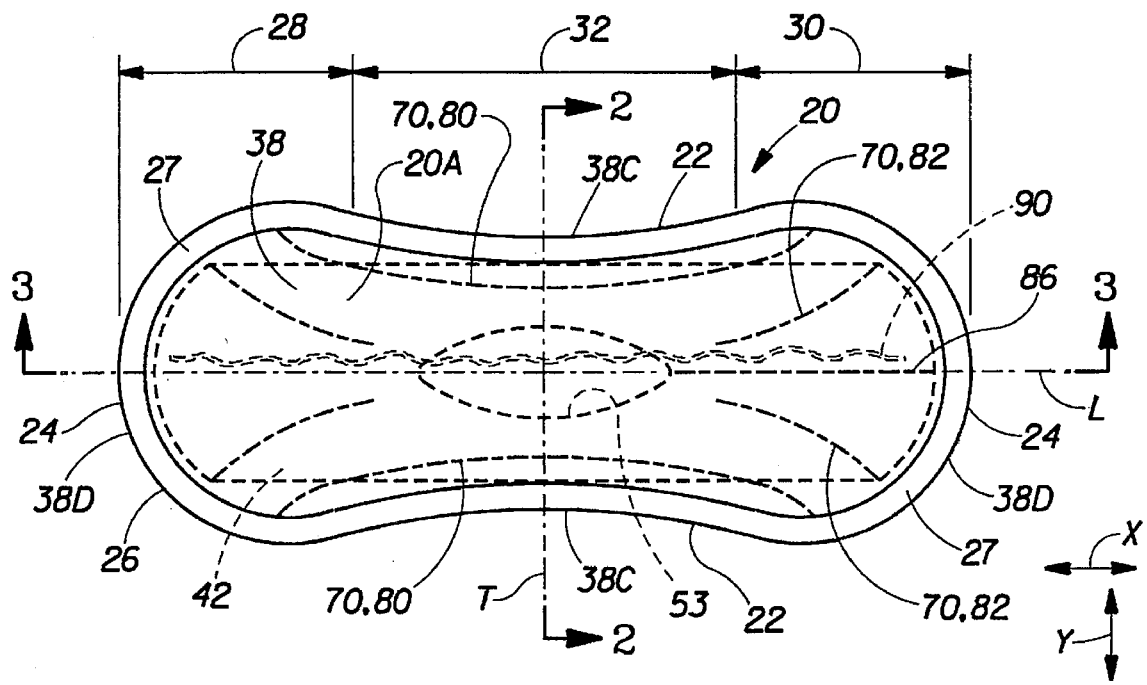
FIG. 1 is a plan view of a preferred sanitary napkin according to the present invention.

The sanitary napkin 20 has two surfaces, a body-contacting surface or "body surface" 20A and a garment surface 20B. The sanitary napkin 20 is shown in FIG. 1 as viewed from its body surface 20A. The body surface 20A is intended to be worn adjacent to the body of the wearer while the garment surface 20B (shown in FIG. 2) is on the opposite side and is intended to be placed adjacent to the wearer's undergarments when the sanitary napkin 20 is worn.

The sanitary napkin 20 has two centerlines, a longitudinal centerline, L, and a transverse centerline, T. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable, and refer to a line, axis or direction which lies within the plane of the sanitary napkin 20 that is generally perpendicular to the longitudinal direction.

FIG. 1 also shows that the sanitary napkin 20 has a periphery 26 which is defined by the outer edges of the sanitary napkin 20 in which the longitudinal edges (or "side edges") are designated 22 and the end edges (or "ends") are designated 24, and the corners of the sanitary napkin are designated 27. The sanitary napkin has two end regions, which are designated first end region 28 and second end region 30. A central region 32 is disposed between the end regions 28 and 30. The end regions 28 and 30 extend outwardly from the edges of the central region 32 about ⅛ to about ⅓ of the length of the sanitary napkin. A detailed description of the central region 32 and the two end regions 28 and 30 is contained in U.S. Pat. No. 4,690,680 issued to Higgins on Sep. 1, 1987.

Figure 2:
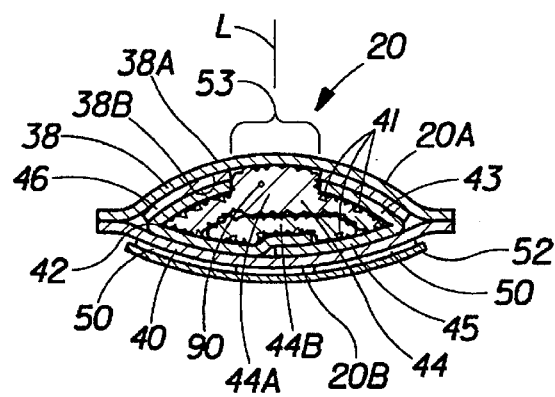
FIG. 2 is an enlarged cross section of the sanitary napkin shown in FIG. 1 taken along line 2—2.
Figure 3:
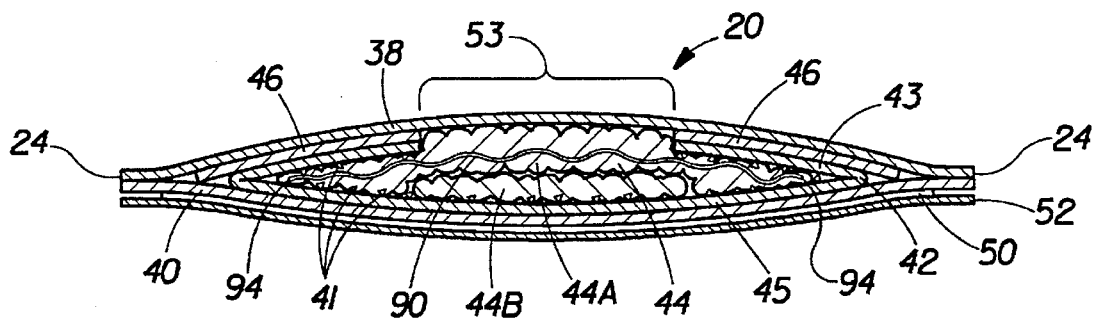
FIG. 3 is a cross section of the sanitary napkin shown in FIG. 1 taken along line 3—3.

The sanitary napkin 20, as shown in FIGS. 1–3, has a component with a window that has a body-conforming acquisition element positioned therein. As shown in FIG. 2, the sanitary napkin 20 preferably comprises a liquid pervious topsheet 38, a liquid impervious backsheet 40 joined to the topsheet 38, and an absorbent core 42 positioned between the topsheet 38 and the backsheet 40. The sanitary napkin preferably also has a wicking layer or secondary topsheet 46 positioned between the topsheet and absorbent core. In a preferred embodiment, the core comprises an upper portion 43 facing the topsheet, a lower portion 45 facing the backsheet, and an intermediate portion 41 positioned between the upper and lower portions. The upper portion 43 of the core and the wicking layer 46 both have a window 53 cut therein. The acquisition/distribution component 44 is positioned so that at least part of it lies in the opening defined by the window 53. The acquisition/distribution component 44 preferably comprises a wet and dry resilient material. One suitable resilient material comprises longitudinally-oriented capillary channel fibers. (i.e., fibers having intra-fiber capillary channels, especially on their exterior surfaces) 90 in the form of a staple sliver of fibers (i.e., a loosely gathered or entangled bundle of fibers of a particular length).

The sanitary napkin 20 can also be provided with one or more additional layers or components. These include a nonwoven layer 48 (See FIG. 6) positioned between the absorbent core 42 and the backsheet 40. The nonwoven layer 48 serves to keep the material of the core 42 from tearing particularly when (the core is comprised of cross-linked cellulose fibers and) the layers of the sanitary napkin are stitched together. The sanitary napkin 20 may also include at least one panty fastener, such as panty fastening adhesive strips 50 (shown in FIGS. 2 and 6). An optional release paper 52 may cover the adhesive strips 50. This keeps the adhesives 50 from sticking to surfaces other than the crotch portion of the undergarment prior to use of the sanitary napkin 20.

The sanitary napkin 20 of the present invention can be constructed generally in accordance with the disclosures of the Capillary Channel Fiber and the Curved Bun patent applications. The acquisition/distribution component (such as the sliver of capillary channel fibers), however, must be placed so that at least part of the acquisition/distribution component lies in a window 53 cut in the upper portion of the core and any overlying wicking layer as taught herein. The remaining portions of the sanitary napkin may otherwise have similar features (e.g., curvature, bending axes, ability to decouple from the wearer's panties, central region and end region caliper and flexibility, body fit, etc.) as the sanitary napkins described in the Capillary Channel Fiber and Curved Bun patent applications. Preferably, however, the first pair of bending axes 80 that are located laterally outboard of the window 53 adjacent the longitudinal edges 22 of the sanitary napkin extend further (i.e., past the extent of the window) into the end regions 28 and 30 of the sanitary napkin of the present invention than the first pair of bending axes described in the Curved Bun patent applications. This assists the sanitary napkin in assuming the desired in-use configuration described in greater detail below.

In addition, the sanitary napkin of the present invention (as in the case of the sanitary napkins described in the Curved Bun patent applications) can also be provided with an optional third type of bending axis that runs along at least a portion of the longitudinal centerline (such as in the back region 30 of the sanitary napkin to assist the back region in bending upward into an inverted "V"-shaped configuration in the area of the wearer's gluteal groove (i.e., the crevice between the wearer's buttocks)). This additional bending axis can be formed by any of the means described in the Curved Bun patent applications.

There are several advantages provided by the sanitary napkin of the present invention. The placement of the acquisition/distribution component in the window provides a less obtrusive structure than the sanitary napkins described in the Curved Bun patent publications in which a bun of capillary channel fibers forms a permanent surface discontinuity (in the form of a hump) on the body surface of the sanitary napkin. The sanitary napkin of the present invention differs in that it provides a relatively flat body surface prior to the application of lateral compressive forces on the sanitary napkin. It is also believed that this may make the sanitary napkin of the present invention have the appearance of being more comfortable when the wearer takes the sanitary napkin out of the package prior to wear due to the absence of the surface discontinuity provided by the hump.

Figure 4:
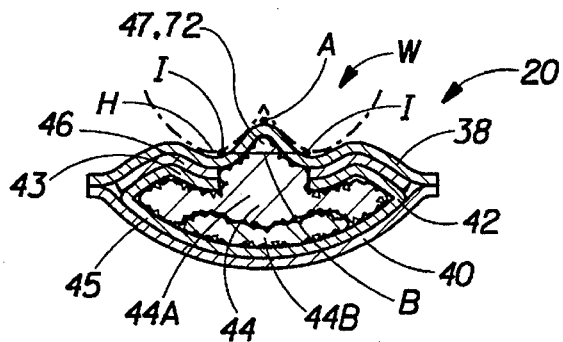
FIG. 4 is a cross-sectional view similar to that of FIG. 2 showing the sanitary napkin with its acquisition/distribution component in a compressed configuration in relation to the wearer's body.

The placement of the acquisition/distribution component in the window also provides a structure having a shape that may more closely fit the wearer's labia majora. This is believed to allow the acquisition/distribution component to be placed in even closer contact with the wearer's body than the capillary channel fiber bun described in the Capillary Channel Fiber Bun applications which may result in improved acquisition of bodily exudates. FIG. 4 shows that the acquisition/distribution component assumes a more narrow triangularly-shaped wedge configuration, (or more preferably, a cusp-shaped configuration) in the area of the wearer's labia majora (so that it closely follows the slope of the labia majora) when it is compressed during wear.

Figure 4A:
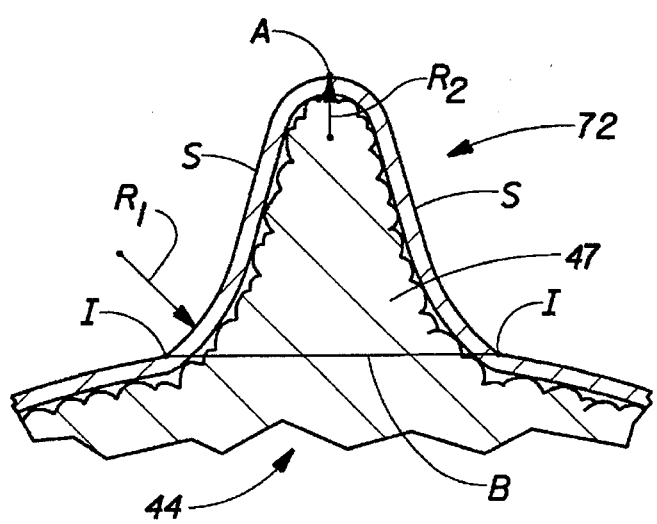
FIG. 4A is an enlarged cross-sectional view of the hump formed by the acquisition/distribution component shown in FIG. 4.

FIG. 4A shows this preferred cross-sectional shape in greater detail. (FIG. 4A, however, differs somewhat from FIG. 4 in that the portions of the sanitary napkin laterally outward from the hump form a convex curve, rather than the concave curve shown in FIG. 4. This simply shows that other curvatures from which the hump projects are possible.) FIG. 4A shows that the sides, S, of the hump 72 formed by the upper portion 47 of the acquisition/distribution component 44 begin at the inflection points I at the base of the hump, B. The sides of the hump 72 can be relatively planar (that is, their cross-sectional configuration can be defined by relatively straight lines), or they can be defined by curved surfaces. If the sides, S, of the hump 72 are curved, individual portions of the surfaces can be curved either concave or convex upward. Preferably, if curved, the sides are only slightly curved with relation to the curvature of the top of the hump. The sides of the hump 72 can have a radius of curvature, such as $R_1$. (The radius of curvature of the sides of the hump may, however, change from the base of the hump to the apex, A, of the hump.) In the preferred embodiment shown in FIG. 4A, the sides, S, of the hump are curved slightly concave upward to follow the slope of the labia majora, and they change to a convex upward curvature having a smaller radius of curvature $R_2$ at the top of the hump.

Figure 5:
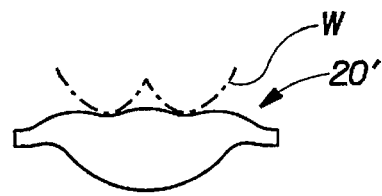
FIG. 5 is a cross-sectional view similar to FIG. 4 which shows the more rounded configuration the body surface of a sanitary napkin having a tufted bundle (or bun) of fibers may have by way of comparison.

This can be compared to FIG. 5 which shows (possibly in a somewhat exaggerated fashion) the more rounded configuration a sanitary napkin 20' having a tufted bundle of fibers or bun may have. The closer fit of the acquisition/ distribution component of the present invention adjacent to the wearer's labia majora may be used to allow the acquisition/distribution component to more readily intercept menses as they leave the wearer's body. It also may have a tendency to reduce the chances for the formation of gaps between the body surface 20A of the sanitary napkin and the labia majora, which gaps may be large enough to permit menses to flow through toward the edges of the sanitary napkin. The extension of the first type of bending axes 80 is believed to enhance the desired cusp shaped configuration by allowing the sanitary napkin to form longer and deeper creases along these axes during wear. This assists in producing a narrower hump for improved fit in the space between the wearer's labia majora.

The sanitary napkin 20 is ideally capable of continuous dynamic adjustment during wear to provide sustained close fit against the wearer's body. The fit in the space between the wearer's labia is enhanced when the acquisition/distribution component is formed from resilient materials, such as capillary channel fibers. Preferably, the materials forming the acquisition/distribution component are both resilient when wet and dry. The resiliency allows the acquisition/ distribution component to adapt to changes in the size of the space between the wearer's labia more readily when the wearer moves about.

Another advantage of the present invention is that the use of the window provides an area in the center of the sanitary napkin where core material has been eliminated. The elimination of the core material in the window area may be used to manipulate the capillary gradient of the sanitary napkin. The elimination of core material promotes draining of exudates received in the central region 32 of the sanitary napkin toward the end regions 28 and 30 by creating a space within the window that is surrounded by the higher suction core material.

Still another advantage of the present invention is that it is believed that the sanitary napkin of the present invention easier to make than the sanitary napkins described in the Capillary Channel Fiber Bun applications. This is due to the fact that it is not necessary to provide a structure where the ends of a batt of capillary channel fibers are inserted within the absorbent core, while other portions of the batt of fibers, such as those portions in the center of the batt, are pulled through a slit in the top of the core to form a bun. The components of the sanitary napkin 20 of the present invention can instead be assembled in a more simple "lay down" process. Due to the presence of the window, the sanitary napkin of the present invention still provides advantages similar to that of the sanitary napkin having a capillary channel fiber bun. However, this can be done at a lower cost in the case of the present invention.

The individual components of the sanitary napkin will now be looked at in greater detail.

2. The Individual Components of the Sanitary Napkin.

A. The Topsheet.

The topsheet 38, as shown in FIGS. 1–3, is the component which is intended to be oriented towards and contact the body of the wearer to receive bodily discharges.

The topsheet 38 is liquid pervious and should be flexible and non-irritating to the skin. As used herein the term "flexible" refers to materials which are compliant and readily conform to the shape of the body or respond by easily deforming in the presence of external forces. The topsheet 38 should exhibit good strikethrough and low rewet characteristics, permitting bodily discharges to rapidly penetrate the thickness of the topsheet 38 and move into the absorbent core 42, but not flow back through the topsheet 38 to the skin of the wearer. Preferably, the topsheet 38 is not noisy, to provide discretion for the wearer. The topsheet 38 should be sanitary, clean in appearance and somewhat opaque to hide bodily discharges collected in and absorbed by the absorbent core 42.

FIG. 2 shows that the topsheet 38 has two sides (or faces or surfaces), including a body-facing side 38A and a garment-facing side (or core-facing side) 38B. The body-facing side 38A of the topsheet 38 generally forms at least a portion of the body-contacting surface ("body surface") 20A of the sanitary napkin 20. The topsheet 38 has, as shown in FIG. 1, two longitudinal edges 38C and two end edges 38D.

(A similar numbering system applies to the other components of the sanitary napkin. That is, the side of the component facing the wearer's body can be designated by the number of the component and a reference letter "A". The side facing the wearer's undergarments can be designated by the number of the component and the letter "B". The side and end edges can be designated by the number of the component and the reference letters "C" and "D" respectively.)

A suitable topsheet 38 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers.

A preferred topsheet 38 comprises an apertured formed film. Apertured formed films are preferred for the topsheet because they are pervious to body exudates, yet non-absorbent, and have a reduced tendency to allow liquids to pass back through and rewet the wearer's skin. Thus, the surface of the formed film which is in contact with the body remains dry, thereby reducing body soiling and creating a more comfortable feel for the wearer.

Suitable formed films are described in U.S. Pat. No. 3,929,135 issued to Thompson on Dec. 30, 1975; U.S. Pat. No. 4,324,246 issued to Mullane, et al. on Apr. 13, 1982; U.S. Pat. No. 4,342,314 issued to Radel. et al. on Aug. 3, 1982; U.S. Pat. No. 4,463,045 issued to Ahr et al. on Jul. 31, 1984; U.S. Pat. No. 4,629,643 issued to Curro, et al. on Dec. 16, 1986; and U.S. Pat. No. 5,006,394 issued to Baird on Apr. 9, 1991. The preferred topsheet for the present invention is the formed film described in one or more of the above patents and marketed on sanitary napkins by The Procter & Gamble Company as "DRI-WEAVE".

In a preferred embodiment, the topsheet 38 is hydrophilic so that liquids will transfer through the topsheet 38 faster than if it was not hydrophilic. This will diminish the likelihood that body exudates will flow off the topsheet rather than being absorbed by the absorbent core. Such topsheets (as well as fibrous topsheets) can be rendered hydrophilic by treating them with surfactants. Suitable methods of applying surfactants are described in U.S. Pat. Nos. 4,950,254 and 5,009,653 issued to Osborn.

B. The Absorbent Core.

(1) General.

The absorbent core 42 is an absorbent means which is capable of absorbing or retaining liquids such as vaginal fluids (e.g., menses) and other certain body exudates. As shown in FIGS. 1–3, the absorbent core 42 has a body surface, a garment surface, side edges, and end edges.

The absorbent core 42 may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles.

Suitable materials for the absorbent core 42 include but are not limited to: comminuted wood pulp, which is generally referred to as airfelt; creped cellulose wadding; tissue including tissue wraps and tissue laminates; synthetic fibers, especially polymeric fibers, such as crimped polyester fibers; meltblown polymers including coform; chemically stiffened, modified or cross-linked cellulosic fibers; fibers have intra-fiber capillary channels preferably on their exterior surfaces (capillary channel fibers); peat moss; absorbent foams; absorbent sponges; superabsorbent hydrogel-forming polymeric gelling agents; or any equivalent materials or combination of materials, or mixtures of these materials.

Polymeric gelling agents are particularly preferred absorbent materials for use in the absorbent core 42. Polymeric gelling agents are those materials which, upon contact with fluids (i.e., liquids) such as water or body fluids, imbibe such fluids and thereby form hydrogels. In this manner, fluid discharged into the absorbent core 42 can be acquired and held by the polymeric gelling agent, thereby providing the absorbent articles described herein with enhanced absorbent capacity and/or improved fluid retention performance. Suitable absorbent gelling materials are described in U.S. Pat. No. Re. 32,649 issued Apr. 19, 1988 to Brandt et al. and U.S. Pat. No. 5,102,597 issued to Roe, et al. on Apr. 7, 1992. A suitable laminate of absorbent gelling materials and tissue may be purchased from Grain Processing Corporation of Muscatine, Iowa under Model Number L535.

Suitable cross-linked cellulose fibers and suitable capillary channel fibers are described in greater detail in the patent publications and patent applications described in subsection 2B(2) below. Suitable foam materials are described in U.S. Pat. No. 5,147,345 entitled "High Efficiency Absorbent Articles for Incontinence Mangagement" issued to Young, et al. on Sep. 15, 1992 and in PCT Publication No. WO 93/04113 entitled "Method for hydrophilizing Absorbent Foam Materials" published in the name of DesMarais on Mar. 4, 1993.

The configuration and construction of the absorbent core 42 may be varied (e.g., the absorbent core may have: varying caliper zones (e.g., the core may be profiled so as to be thicker in the center); hydrophilic gradients; superabsorbent gradients, or lower density and lower average basis weight acquisition zones; or it may comprise one or more layers or structures). The total absorbent capacity of the absorbent core 42 should, however, be compatible with the design loading and the intended use of the sanitary napkin 20. Further, the size and absorbent capacity of the absorbent core 42 may be varied to accommodate different uses such as incontinence pads, pantiliners, regular sanitary napkins, or overnight sanitary napkins.

Examples of absorbent structures suitable for use as the absorbent core of the present invention are described in: U.S. Pat. No. 4,578,068 entitled "Absorbent Laminate Structure" issued to Kramer, et al. on Mar. 25, 1986; U.S. Pat. No. 4,610,678 entitled "High-Density Absorbent Structures" issued to Weisman et al. on Sep. 9, 1986; U.S. Pat. No. 4,640,810 entitled "System for Producing an Airlaid Web" issued to Laursen, et al. Feb. 3, 1987 (or airlaid structures made by different processes); U.S. Pat. No. 4,834,735 entitled "High Density Absorbent Members Having Lower Density and Lower Basis Weight Acquisition Zones", issued to Alemany et al. on May 30, 1989; U.S. Pat. Nos. 4,950,264 and 5,009,653 entitled "Thin, Flexible Sanitary Napkin" issued to Osborn on Aug. 21, 1990 and Apr. 23, 1991; European Patent Application No. 0 198 683, published Oct. 22, 1986 in the name of Duenk, et al.; and in U.S. patent application Ser. No. 07/810,774 and its continuation-in-part, Ser. No. 07/944,764 both entitled "Absorbent Article Having Fused Layers" filed in the name of Cree, et al. on Dec. 17, 1991 and Sep. 14, 1992, respectively.

(2) The Cross-Linked Cellulose Fiber Laminate Core.

A preferred embodiment of the absorbent core 42 comprises the laminate structure shown in FIGS. 1-4. The laminate is comprised of one or more layers of superabsorbent polymeric material (or absorbent gelling material) and one or more sheets or webs of cross-linked cellulosic fibers. Preferably, as shown in FIGS. 1 and 6, the absorbent gelling material is situated on the inside of two layers of cross-linked cellulosic fibers.

Suitable cross-linked cellulose fibers for the absorbent core are described in U.S. Pat. No. 4,822,543, issued Apr. 18, 1989 to Dean, et al.; U.S. Pat. No. 4,888,093, issued Dec. 19, 1989 to Cook, et al.; U.S. Pat. No. 4,889,595, issued Dec. 26, 1989 to Schoggen, et al.; U.S. Pat. No. 4,898,642, issued Feb. 6, 1990 to Moore, et al.; U.S. Pat. No. 4,935,022 issued Jun. 19, 1990 to Lash et al.; and U.S. Pat. No. 5,183,707 issued Feb. 2, 1993 to Herron, et al.; U.S. Pat. No. 5,217,445 issued Jun. 8, 1993 to Young, et al.; in EPO Patent Application Publication Nos. 0 427 316 A2 and 0 427 317 A2 published in the name of Herron, et al. on May 15, 1991; and EPO Patent Application Publication No. 0 429 112 A2 published in the name of Herron, et al. on May 29, 1991.

Figure 6:
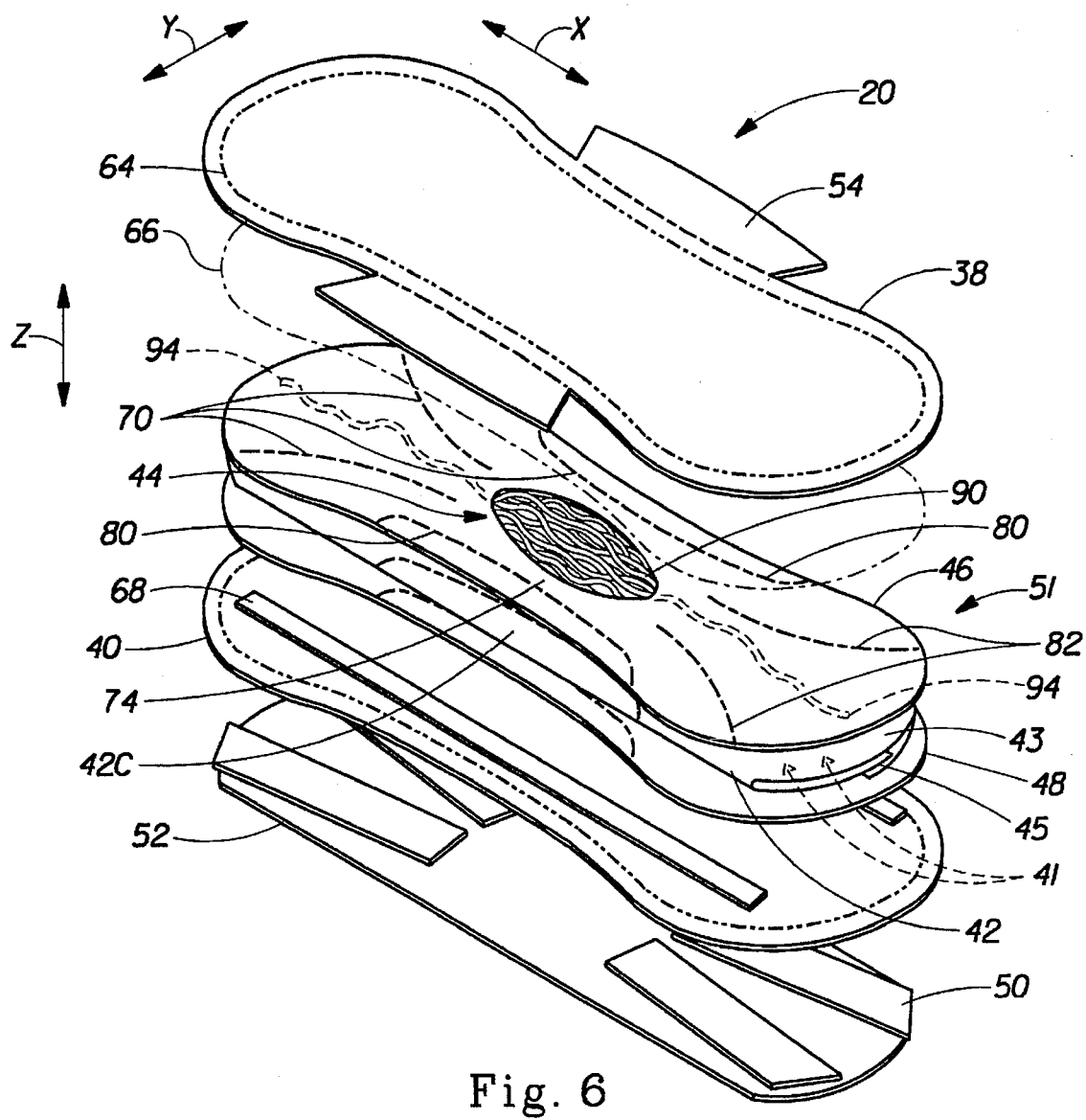
FIG. 6 is an exploded perspective view showing the assembly of one version of the sanitary napkin shown in FIG. 1.

The cross-linked cellulosic fibers in the embodiment shown in FIG. 6, comprise a single sheet that has particles 41 of absorbent gelling material affixed to one side thereof (such as by gluing) which is then folded with that side facing inward so that it in effect wraps the particles of absorbent gelling material. The sheet is wrapped so that it appears as having an "e" (or reverse "e" configuration) when viewed from the end. The wrapped sheet forms an upper layer 43 and a lower layer 45. In alternative embodiments, the laminate can be formed in many other manners, such as by providing separate webs of cross-linked cellulosic material (or other absorbent material or materials) for the different layers of the absorbent core laminate rather than a single sheet, or by providing it with additional layers.

C. The Backsheet.

The backsheet 40 prevents the exudates absorbed and contained in the absorbent core 42 from wetting articles which contact the sanitary napkin 20 such as pants, pajamas and undergarments. The backsheet 40 is impervious to liquids (e.g., menses and/or urine). The backsheet 40 is preferably manufactured from a thin plastic film, although other flexible liquid impervious materials may also be used.

The backsheet 40 may comprise a woven or nonwoven material, polymeric films such as thermoplastic films of polyethylene or polypropylene, or composite materials such as a film-coated nonwoven material. Preferably, the backsheet 40 is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Tredegar Film Products of Terre Haute, Indiana, under the designation XP-39385.

The backsheet 40 is preferably embossed and/or matte finished to provide a more clothlike appearance. Further, the backsheet 40 may permit vapors to escape from the absorbent core 42 (i.e., the backsheet 40 may be breathable) while still preventing exudates from passing through the backsheet 40. Flushable or biodegradable backsheets can also be used, e.g., such as with pantiliner devices of the type described herein.

D. The Acquisition/Distribution Component and Placement of the Same in the Window.

(1) The Acquisition/Distribution Component.

The acquisition/distribution component 44 is intended to provide the sanitary napkin 20 with at least liquid acquisition capabilities, and preferably also with liquid transport and distribution capabilities. The acquisition/distribution component 44 may, therefore, be referred to as an "acquisition component", a "transport component", a "liquid acquisition/distribution component", or by some other suitable name that describes its function. For the purposes of the present invention, an absorbent article has the type of acquisition component specified if it has a component with any capability for performing the function specified by its name (i.e., an "acquisition component" need only be capable of acquiring liquids, while an "acquisition/distribution component" both acquires and distributes liquids).

FIGS. 1–3 show that the acquisition/distribution component 44 is preferably positioned between the topsheet 38 and at least part of the absorbent core 42. (That is, the acquisition/distribution component lies below the topsheet, but portions of the acquisition/distribution component 44 may lie above the core 42 and other portions may be positioned within the core 42.) The acquisition/distribution component 44 is preferably centered along the longitudinal centerline of the sanitary napkin.

The acquisition/distribution component 44 can also be centered along the transverse centerline of the sanitary napkin. In alternative embodiments, the acquisition/distribution component can be offset from the transverse centerline (that is, positioned forward or rearward of the transverse centerline). If the acquisition/distribution component 44 is offset from the transverse centerline, it is preferably positioned so that it at least partially lies in the central region 32 of the sanitary napkin 20.

The sanitary napkin 20 may have an acquisition/distribution component 44 that comprises any of those materials specified as being suitable for use in the absorbent core 42. Preferably, however, the acquisition/distribution component 44 comprises a material that is more resilient than airfelt (which is often used as an absorbent core material). Suitable resilient materials include, but are not limited to: capillary channel fibers; chemically modified, cross-linked cellulosic fibers; polyesters; rayons; orlons; foams; and surfactant treated polyolefin fibrous materials. The materials described herein can also be formed into laminates with superabsorbent polymer material in the form of particles or fibers or mixed with superabsorbent polymer material. Suitable superabsorbent fibers are those formerly manufactured by Arco Chemical Company of Newton Square, Pa. under the trademark FIBERSORB and those currently manufactured by Courtaulds, Ltd., West Midlands, England. (Superabsorbent fibers are discussed more fully in U.S. Pat. No. 4,855,179, issued Aug. 8, 1989 to Bourland, et al.)

FIGS. 1–4 show one preferred embodiment in which the acquisition/distribution component 44 is comprised of capillary channel fibers 90. Suitable capillary channel fibers, including fiber morphology, configuration, length, channel shapes and sizes, surface properties, and preparation and treatments, are described in the "Capillary Channel Fiber" and "Curved Bun" patent publication incorporated by reference herein.

Suitable capillary channel fibers are also described in EPO Patent Application 0 391 814 published Oct. 10, 1990; U.S. Continuation-In-Part Application entitled "Fibers Capable of Spontaneously Transporting Fluids", Ser. No. 07/736,267, filed Jul. 23, 1991, Inventors Phillips, Jones, et al., Eastman Chemical Company; U.S. Pat. No. 5,200,248 entitled "Open Capillary Channel Structures, Improved Process for Making Capillary Channel Structures, and Extrusion Die for Use Therein" issued to Thompson and Krautter on Apr. 6, 1993; and, U.S. patent application Ser. No. 07/918,174 entitled "Spinerette Orifices and Filament Cross-Sections With Stabilizing Legs Therefrom", filed in the name of Phillips, et al. on Jul. 23, 1992.

The capillary channel fibers 90 can be provided in several possible structural arrangements for use in the absorbent article. In the preferred embodiment shown in FIGS. 1–4, the capillary channel fibers are in the form of at least one staple sliver of fibers 44 (i.e., a loosely gathered or entangled bundle of fibers of a particular length) that has been cut from a tow of fibers (that is, a continuous length bundle of generally relatively long untwisted fibers).

Preferably, as shown in FIG. 2, the capillary channel fibers 90 are provided in the form of two fiber slivers. These comprise an upper sliver 44A comprised of about 1.2 grams of 6 inch (15 cm) long fibers which is about 7 inches (17.8 cm) in length, and a lower sliver 44B comprised of about 0.3 grams of fibers cut from a tow of fibers that has the same characteristics as that used to form the upper sliver, but is cut into a 3 inch (7.6 cm) sliver. The lower sliver 44B is used in the embodiment shown in FIGS. 1–4 to provide the sanitary napkin 20 with a profiled body-contacting shape, particularly in the area of the window 53 when the sanitary napkin is compressed, and to provide extra liquid transporting capability in the portion of the sanitary napkin that will lie under the vaginal opening.

The upper sliver 44A can simply be laid down on top of the lower sliver 44B without securing the slivers together. Alternatively, the upper and lower slivers can be joined by any of the mechanisms specified herein for joining the slivers to the topsheet and absorbent core, respectively. In one preferred embodiment, the slivers can be held together between two layers of material, such as between an optional secondary topsheet 46 and a nonwoven layer 48 (shown in FIG. 6), by bonds that pass from the secondary topsheet 46 all the way through to the nonwoven layer 48.

FIGS. 2 and 3 show that in a preferred embodiment, the slivers of fibers 44A and 44B run lengthwise (i.e., in the longitudinal direction) under the upper layer 43 of the absorbent core 42. The positioning of the slivers 44A and 44B results in part of the slivers lying within the window 53 that is provided in both the upper layer 43 of the core and the overlying wicking layer 46. The slivers of capillary channel fibers, and the fibers therein, can, however, be positioned in other locations and oriented in other directions. (The slivers 44A and 44B also may hereinafter be referred to herein collectively simply as the "sliver of capillary channel fibers" or "sliver" 44 for simplicity.)

By providing capillary channel fibers 90 that are oriented in the longitudinal direction, fluid flow in the longitudinal direction is promoted. This makes greater use of the overall absorbent capacity of the sanitary napkin. Further, by orienting the capillary channel fibers of the sliver 44 in the longitudinal direction, fluid flow in the transverse direction is controlled, thereby minimizing, or even entirely avoiding, leakage of liquids from the longitudinal side edges 22 of the sanitary napkin. In addition, the capillary channel fibers provide inherent advantages since the capillarity of the sliver 44 of the present invention resides in the capillary channel fibers 90 themselves, rather than in inter-fiber spacings, capillarity is not lost when fiber-fiber spacings become displaced. The capillary channel fiber sliver 44 of the present invention provides its liquid drawing and directing functions even when the sliver 44 is soft, fluffy and comfortable to the wearer, in contrast to compact, dense and relatively stiff materials which function by inter-fiber capillary action.

The sliver 44 of capillary channel fibers is preferably kept in close contact with the overlying topsheet 38. This can be achieved by a number of suitable mechanisms. These include, but are not limited to bonding the sliver 44 to the topsheet 38 such as by adhesives, ultrasonics, and the like; or, by the use of tensional forces. The contact between the topsheet 38 and the capillary channel fibers may be close enough so that some of the capillary channel fibers 90 extend into the orifices of the topsheet. A detailed description of preferred adhesives and adhesive application configurations for attaching capillary channel fibers to a topsheet is found in the patents incorporated by reference herein.

It is also preferable that there be close contact between the capillary channel fibers 90 and the absorbent core 42 in order to efficiently transfer liquids to the absorbent core 42. This close contact can also be achieved in a number of ways. These include, but are not limited to, the use of adhesives, ultrasonic bonds, by tensional forces, by providing a toughened surface of the absorbent core, or by needle-punching, or otherwise inserting some of the capillary channel fibers into the absorbent core.

Thus, in a highly preferred mode there is an interconnecting network between topsheet, the sliver of capillary channel fibers 44, and the underlying absorbent core. This allows liquids to efficiently proceed through the topsheet 38, and to move along and through the capillary channel sliver 44 and into the absorbent core 42. This interconnection is preferably maintained even in the face of in-use stresses such as moisture, mechanical shear, and pressure-relaxation associated with physical movements of the wearer.

The absorbent core 42 preferably serves as a reservoir for fluids which are transferred from the capillary channel fiber structure into the core. Cores typically exhibit high suctional forces which tend to draw away fluids from the capillary channel fibers and into the core for ultimate storage. This is precisely the intended effect. Thus, as fluid proceeds into the article, it encounters the capillary channel fiber network, which distributes the fluid and then surrenders it to the underlying absorbent core, thereby at least partially "renewing" the capillary channel fiber network for the next infusion of fluid.

The sliver of capillary channel fibers 44 has two ends designated 94. The ends 94 preferably extend along the longitudinal centerline L of the sanitary napkin 20. The ends 94 are in fluid (i.e., liquid) transporting contact with the absorbent core laminate. The ends 94 of the sliver 44 serve as conduits for transporting liquids directly to the absorbent core 42. Even more preferably, the ends 94 are capable of transporting liquids to the interior of the absorbent core 42. This provides the sanitary napkin 20 with another advantage.

Generally, when exudates are simply deposited on top of an absorbent component, such as the absorbent core 42, they can be absorbed relatively readily along the top surface of the absorbent component. However, liquids tend to remain in and fill the upper parts of the core first. The saturation of upper regions of the core blocks the transportation of exudates to the lower regions of the core. The placement of the ends 94 of the sliver within the core 42 reduces the potential for this problem to occur. The placement of the ends 94 within the core 42 eliminates the need for liquids to travel through one part of an absorbent storage component like the core 42 to get the place where available absorbent capacity exists.

The construction of the sanitary napkin 20 described above is only one of many possible arrangements of the acquisition/distribution component. As in the case of the absorbent articles described in the "Curved Bun" patent applications, many other suitable arrangements of components are possible if the principles described herein are followed. For instance, the ends 94 (or other portions) of the sliver of capillary channel fibers 44 could be placed in contact with the absorbent core 42 in a number of different ways. The ends could, for instance, be: (1) placed entirely within a window in one of more components (and not behind the window); (2) surrounded by the other components of the absorbent core (particularly, those components with higher capillarity); (3) commingled or integrated into the other components; (4) placed between two or more layers of the other components, such as described immediately above; (5) placed under at least one other layer; or, (6) placed on top of the other components.

The mechanism by which the acquisition/distribution component 44 operates to adjust to the wearer's body is described below. When the sanitary napkin is subjected to laterally inwardly-oriented compressive forces, the sliver (or other acquisition/distribution component) 44 preferably comprises an upper portion 47 that forms a hump 72 that extends above the main absorbent component of the sanitary napkin, the absorbent core 42. This upper portion 47 is similar to, but preferably more narrow than the bun described in the "Curved Bun" patent applications. The upper portion 47 of the acquisition/distribution component 44 can then be positioned in close contact with the wearer' body. Even more advantageously, the upper portion 47 of the liquid acquisition/distribution component 44 can be of such a size and shape that it can fit at least partially within the space between the wearer's labia. This allows it to more readily intercept exudates that leave the wearer's body.

The acquisition/distribution component 44 preferably has several additional key properties. The acquisition/distribution component 44 should be somewhat compressible for added comfort. Preferably, the acquisition/distribution component 44 compresses to less than or equal to about 90%, more preferably less than or equal to about 85%, still more preferably less than or equal to about 80% of its original caliper. (This measurement, and the rest of the measurements specified herein relating to resiliency should be carried out on the acquisition component when it is in place in the entire absorbent article.)

The acquisition/distribution component 44 is preferably also comprised of a resilient material. The term "resilient", as used herein, means that when the material is compressed under a load of 0.25 psi. for 5 seconds and the compressive forces cause a reduction in the dimension of the material in the direction of the compressive forces, the material returns to at least about 50% of its uncompressed dimension after the load is removed. Preferably, the acquisition/distribution recovers to greater than or equal to about 80%, more preferably about 85%, more preferably about 90%, still more preferably about 95%, and most preferably about 100% of its compressed caliper when measured according to the Caliper Recovery Test described in Section 5 of this specification.

Preferably, the material chosen for the acquisition/distribution component 44 is resilient in the amounts set forth above under wet and dry conditions (i.e., it is wet and dry resilient). Preferably, the denier and strength of the capillary channel fibers 90 are chosen so that the acquisition/distribution component has a ratio of wet:dry caliper of at least about 80%, more preferably at least about 90%. This ensures that the structure will retain its soft and form-fitting qualities in use. In addition, if the acquisition/distribution component 44 is wet resilient, it will not collapse when wetted by bodily discharges and will be able to handle initial, as well as subsequent loadings of bodily fluids. (All percentages, ratios and proportions set out in this specification are by weight, unless otherwise specified.)

(2) The Window in Which the Acquisition/Distribution Component is Placed.

The window 53 shown in FIG. 1 has a longitudinally-oriented elliptical configuration. The window 53 can have many alternative configurations. Such configurations include, but are not limited to ovals, race-track shaped, rectangular, cigar-shaped, and the like configurations.

The window 53 can, depending on its configuration, be as long as the absorbent core 42. The window can have a width that extends up to the width of the core. In the embodiment shown in FIG. 1, however, the width of the window 53 preferably extends only to just inside of the first pair of bending axes 80. In addition, the window preferably does not have a length and width that are both equivalent to those dimensions of the absorbent core because this will provide a hump that is much larger than desired. The length of the window can be made somewhat long (that is, the length of the window can approach the length of the absorbent core) if the window is narrow to provide a hump having a suitable size. (Preferably, the length of the window is less than or equal to about ½ the length of the absorbent core).

In especially preferred embodiments, the dimensions of the window are set so that the acquisition/distribution component deforms into a compressed configuration having dimensions that are capable of fitting between the wearer's labia. In these especially preferred embodiments, the size of the Window is established so that the hump formed by the upper portion of the acquisition/distribution component has approximately the following dimensions: a length (or x-direction dimension) of about 1.5–4 inches (about 4–10 cm), more preferably about 1.5–3 inches (about 4–7.5 cm). The width of the window 53 is preferably chosen so that the hump has a width (or y-direction dimension) at the widest point of its base of greater than or equal to about ⅜ inch (about 1 cm) and less than or equal to about 2 inches (about 5 cm), and most preferably greater than or equal to about ⅜ inch and less than or equal to about 1.5 inches (about 4 cm). The hump is preferably tapered so that the upper portions of the same become narrower the further they are from the base of the hump so that the hump is less than or equal to about ⅜ inch wide halfway between the base and its apex. In one particularly preferred embodiment, the window 53 is in the shape shown in FIG. 1, and is about 2 inches (about 5 cm) long and about 1 inch (about 2.5 cm) wide at its widest point.

In alternative embodiments, the window 53 may be provided through the entire absorbent core 42, rather than only being provided in an upper layer of a layered absorbent core, as in the case of the preferred embodiment shown in the drawings. For instance, a window can also be cut through lower layer of the core shown in the drawings.

Figure 7:
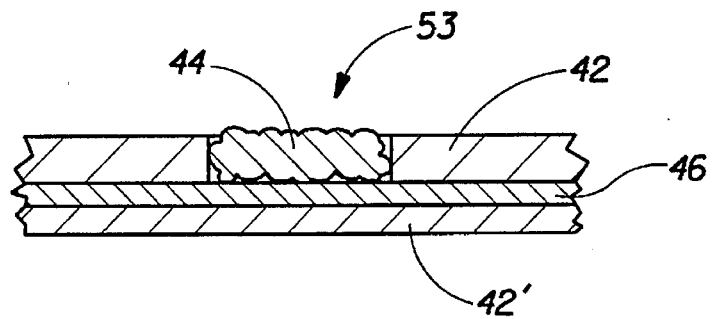
FIG. 7 is a simplified fragmentary cross sectional view of an alternative absorbent core arrangement in which the acquisition/distribution component is located entirely with a window in the core.

In another example, shown in FIG. 7, the absorbent core 42 used in the sanitary napkin can comprise a single layer, such as a layer of airfelt. In one variation of such a single layer embodiment, the layer of airfelt can have a window cut either completely through its thickness (or at cut at least a portion of the way through its thickness), and a mass of resilient fibers can be placed in the center of the window. This can provide a relatively inexpensive alternative construction to the preferred embodiment shown in the drawings. Such an embodiment can be provided with an optional wicking layer 46 beneath the core 42. The embodiment shown in FIG. 7 can also be provided with additional absorbent material 42' beneath this wicking layer. The embodiment shown in FIG. 7 can also be provided with extra fibers (preferably resilient fibers) beneath the window to assist the acquisition/distribution component 44 in the window in deforming upward inuse.

It is also possible in this and any of the other embodiments described throughout this specification, to create an acquisition/distribution component that deforms downward, rather than upward when compressed. Such downward deformation can, for example, be used to provide the sanitary napkin with a cup-like structure under the vaginal orifice. Such embodiments are less preferred, however, because they do not provide a hump that follows the slope of the wearer's labia majora.

Figure 8:
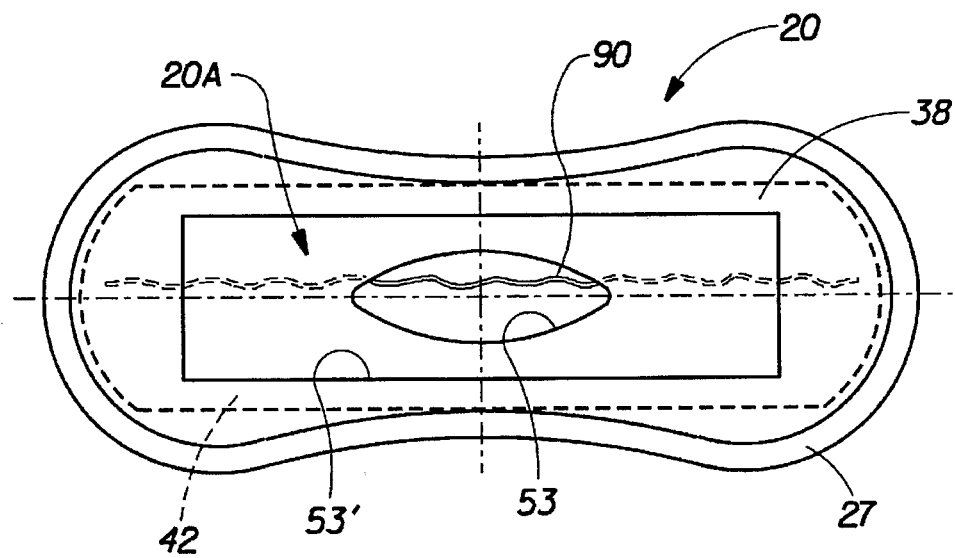
FIG. 8 is a plan view of an alternative sanitary napkin that is also provided with a window in its topsheet.

In another alternative embodiment shown in FIG. 8, the sanitary napkin 20 can also be provided with a window 53' in its topsheet 38. FIG. 8 shows an embodiment in which the window in the secondary topsheet and the upper portion of the core are of the same size and shape and the window 53' in the topsheet is both larger and of a different shape than the window in the secondary topsheet and the upper portion of the core. It should be understood, however, that the windows in the secondary topsheet and the core need not be of the same size and shape. In addition, the window in the topsheet and the window in any other components of the sanitary napkin can be of the same size and shape. In alternative embodiments, the window in the topsheet 53' can be smaller that the window in one or more of the other components. The window 53' in the topsheet is useful in that it provides a structure in which the underlying acquisition/distribution component can be placed in direct contact with the wearer's body over a portion of the body-facing surface 20A of the sanitary napkin. This type of structure is typically preferred when the acquisition/distribution component comprises a material that drains liquids well so that liquids will not tend to rewet the wearer's skin.

(3) The Body-Conforminq Properties of the Acquisition/Distribution Component.

The acquisition/distribution component 44 has an uncompressed configuration (shown in FIGS. 1–3) when the compressive forces supplied by the wearer's thighs are absent. When the acquisition/distribution component 44 is in its uncompressed configuration, it lies relatively flat inside and under the window 53.

FIG. 4 shows that acquisition/distribution component 44, particularly the portion of the acquisition/distribution component located within the window 53, has a compressed configuration when it is subjected to laterally inward compressive forces by the insides of the wearer's thighs. When it is in its compressed configuration, the acquisition/distribution component 44 preferably forms a hump 72 on the body surface of the sanitary napkin that protrudes from the window 53 and conforms to the wearer's body, particularly to the space between the wearer's labia.

The hump formed by compression of the sanitary napkin of the present invention can have any of the properties of the hump described in U.S. patent application Ser. No. 08/007, 207 filed Jan. 22, 1993. When compressed, the sliver 44 of capillary channel fibers forms a hump 72 that preferably has a caliper (or z-direction dimension) of about 2 mm or 3 mm to about 10 mm or 15 mm, or more, and is preferably about 5 mm–10 mm, most preferably about 5 mm–8 mm. The caliper of the hump 72 at its point of maximum elevation is preferably greater than or equal to about 1.5 times the caliper of the surrounding portions of the sanitary napkin. These surrounding regions are the regions of the sanitary napkin to the transverse sides of the hump 72 (the longitudinal side regions) and the regions of the sanitary napkin to the ends of the hump 72 (end regions 28 and 30) of the sanitary napkin. The hump 72 is preferably tapered so that its point of maximum caliper extends less than or equal to about ¾ the width of the hump 72.

Several alternative embodiments of the acquisition/distribution component 44 are discussed below.

(4) Other Alternative and Additional Types of Acquisition/Distribution Components.

In alternative embodiments, rather than being arranged in the form of fiber slivers, the capillary channel fibers, can be arranged in the form of other fiber structures such as nonwoven structures. Particularly suitable nonwoven capillary channel fiber structures include nonwoven structures with capillary channel fibers oriented parallel to the capillary channels. Such structures are described in U.S. patent application Ser. No. 07/943,261 entitled "Fluid Transporting and Retaining Structure" filed in the name of Thompson, et al. on Sep. 10, 1992, (P&G Case 4715).

In addition, other fibers that have channels for transporting liquid on their exterior surfaces are described in European Patent Application Publication Number 0 493 728 A1 published in the name of Meirowitz, et al., on Dec. 17, 1990, and in PCT Publication No. WO 93/07313 entitled "Oriented, Profiled Fibers" published in the name of Hogle, et al. and assigned to 3-M on Apr. 15, 1993.

In other alternative embodiments, the acquisition/distribution component 44 may comprise other types of structures and materials (instead of, or in addition to, capillary channel fiber slivers). These other types of structures and materials include, but are not limited to nonwoven or woven webs of synthetic fibers including polyester, polypropylene, or polyethylene; natural fibers including cotton or cellulose; blends of such fibers; or any equivalent materials or combinations of materials.

The sanitary napkin 20 may also have additional types of acquisition/distribution components or layer(s), such as the secondary topsheet 46, positioned between the topsheet and the absorbent core in the preferred embodiment shown in FIGS. 1–4. Such an additional acquisition layer could be used to distribute body exudates that are deposited longitudinally or laterally outside of the primary acquisition/distribution component (e.g., the sliver 44 of capillary channel fibers) to the absorbent core 42. These other types of acquisition/distribution components, the methods of securing the same in absorbent articles, and the functions served by the same are described in U.S. Pat. Nos. 4,950,264 and 5,009,653 issued to Osborn, and in U.S. patent application Ser. No. 07/810,774, "Absorbent Article Having Fused Layers", filed Dec. 17, 1991 in the names of Cree, et al.

In such alternative embodiments, capillary channel fibers may also be used as the secondary topsheet particularly under a porous (preferably formed-film) topsheet. Thus, the capillary channel fibers draw fluid through the topsheet, thereby leaving the topsheet with a fresh, dry appearance and feel, then surrender the fluid to the underlying acquisition/distribution component and then the absorbent core, and are thus able to continue the process until the core is saturated. The liquid handling characteristics of the components of such a secondary topsheet are described in U.S. application Ser. No. 07/915,286, entitled "Absorbent Articles, Especially Catamenials, Having Improved Fluid Directionality" filed in the names of H. A. Thompson, et al. on Jul. 23, 1992.

E. Fasteners for Attaching the Sanitary Napkin to the Wearer's Panties.

The outwardly-oriented face of the backsheet 40 may, as shown in FIG. 2, further comprise a means for attaching the sanitary napkin 20 to the undergarment of the wearer (such as a fastener) 50.

Fasteners comprising adhesives have been found to work well for this purpose. Any adhesive or glue used in the art for such purposes can be used, with pressure-sensitive adhesives being preferred. Suitable adhesives are Century A-305-IV manufactured by the Century Adhesives Corporation, Instant Lock 34-2823 manufactured by the National Starch Company, 3 Sigma 3153 manufactured by 3 Sigma, and Fuller H-2238ZP manufactured by the H. B. Fuller Co. Suitable adhesive fasteners are also described in U.S. Pat. No. 4,917,697.

The fastener 50 can be in many possible configurations depending on the characteristics desired for the sanitary napkin. Suitable fastener configurations are shown in PCT International Patent Publication No. WO 92/04000 entitled "Shape and Adhesive Fastening Means for an Absorbent Article" published in the name of Papa, et al. on Mar. 19, 1992, in the Capillary Channel Fiber patent applications, the Curved Bun patent applications, and the Extensible Absorbent Article patent applications described in greater detail below. Particularly preferred adhesive fastener configurations for the sanitary napkin shown in FIGS. 1–4 are the modified "X" configuration (which is shown best in FIG. 6) and the "V" and inverted "V"-shaped configuration, both of which allow the central region 32 of the sanitary napkin to "decouple" from the wearer's panties. These preferred adhesive configurations are described in greater detail in PCT Publication No. WO 93/01783 published in the name of Olsen, et al.

In addition, other types of fasteners can be used instead of, or in addition to adhesives. These other types of fasteners are preferably arranged in patterns similar to those in the patent publications referred to above. Such fasteners include, but are not limited to conventional VELCRO hook material, the fasteners described in: U.S. Pat. No. 4,946,527 issued to Battrell on Aug. 7, 1990; U.S. Pat. Nos. 5,058,247 and 5,116,563 issued to Thomas, et al. on Oct. 22, 1991 and May 26, 1992, respectively; and EPO Patent Application Publication No. 0 381 087 published Aug. 8, 1990; or, high coefficient of friction foams and other high coefficient of friction materials in the same category as those described in U.S. Pat. No. 4,166,464 issued to Korpman, U.S. Pat. No. 4,834,739 issued to Linker, III, et al., and U.S. Pat. No. 5,011,480 issued to Gossens, et al.

Before the sanitary napkin 20 is placed in use, if an adhesive fastener is use, the pressure-sensitive adhesive is typically covered with a removable cover strip or release liner 52 in order to keep the adhesive from sticking to a surface other than the crotch portion of the panty prior to use. Suitable release liners are also described in the above-referenced U.S. Pat. No. 4,917,697. Any commercially available release liners commonly used for such purposes can be utilized herein. Non-limiting examples of suitable release liners are BL30MG-A Silox E1/O and BL30MG-A Silox 4P/O both of which are manufactured by the Akrosil Corporation.

In one particularly preferred embodiment, the adhesive fastener 50 is protected with a wrapper that not only covers the adhesive, but also provides both an individually packaged sanitary napkin and a container for disposing the sanitary napkin after use, such as is described in U.S. Pat. No. 4,556,146 issued to Swanson, et al. on Dec. 3, 1985.

The sanitary napkin 20 of the present invention is used by removing any release liner 52 and thereafter placing the sanitary napkin 20 in a panty so that the adhesive (or other fastener) 50 contacts the panty and maintains the sanitary napkin in position within the panty during use.

F. Assembly of the Components of the Sanitary Napkin.

The components of the sanitary napkin such as the topsheet, the backsheet, the absorbent core, and any other components, may be assembled in a variety of well known configurations (including so called "tube" products or side flap products).

The components of the sanitary napkin are preferably assembled in a "sandwich" configuration with the topsheet, backsheet, and absorbent core each comprising a layer and the absorbent core positioned between the topsheet and backsheet. The sanitary napkin embodiment shown in FIGS. 1-3 is preferably assembled similarly to the sanitary napkins described in the "Curved Bun" patent applications. Thus, the sanitary napkin has its components secured with several different types of attachment mechanisms.

As shown in FIG. 6, the components of the sanitary napkin 20 are held together by a perimeter seal 64, a topsheet attachment mechanism, such as topsheet bonding adhesive 66, and a backsheet attachment mechanism, such as backsheet bonding adhesive 68. In addition, the sliver 44 of capillary channel fibers, the secondary topsheet 46, the absorbent core 42, and the nonwoven layer 48 are held together by stitching lines 70 to form a core/nonwoven sheet sandwich. The stitching lines 70 preferably form bending axes 80 and 82 for portions of the sanitary napkin to bend about when the sanitary napkin 20 is worn. These components and features are described in greater detail in the Curved Bun patent applications incorporated by reference herein.

The sanitary napkin of the present invention is not limited to using the types of securement mechanisms shown in FIG. 6, however. The various components of the sanitary napkin 20 may be held together in many other suitable manners. The components of the sanitary napkin 20 can, for instance, be secured together by adhesives, stitching, heat and/or pressure bonds, dynamic mechanical bonds, ultrasonic bonds, intermingling or entanglement of the fibers or other structural elements comprising the components of the sanitary napkin, such as by meltblowing the fibers comprising one component onto another component, or by any other means known in the art. Suitable means for attaching the components of the sanitary napkin are described in the patent applications described above filed in the name of Cree, et al.

G. Alternative Embodiments and Optional Features.

The sanitary napkin 20 may also be provided with a pair of flaps, each of which are adjacent to and extend laterally outward from a side edge of the main body portion of the sanitary napkin. (The main body portion is the portion of the sanitary napkin without the flaps.) The flaps are preferably configured to drape over the edges of the wearer's panties in the crotch region so that they are disposed between the wearer's panties and the wearer's thighs.

Such flaps can serve at least two purposes. First, the flaps help to prevent soiling of the wearer's body and panties by menstrual fluid. Second, the flaps are preferably provided with attachment means on their garment surface so that the flaps can be folded back under the panty and attached to the garment-facing side of the panty. In this way, the flaps serve to keep the sanitary napkin 20 properly positioned in the panty. Alternatively, the flaps may be attached to each other on the underside of the panty by the attachment means with or without also being affixed to the panty.

A number of sanitary napkins having flaps suitable or adaptable for use with the sanitary napkin 20 of the present invention are known. Such flaps are disclosed in U.S. Pat. No. 4,285,343 entitled "Sanitary Napkin", issued to McNair on Aug. 25, 1981; U.S. Pat. No. 4,589,876 entitled "Sanitary Napkin", issued to Van Tilburg on May 20, 1986; U.S. Pat. No. 4,608,047 entitled "Sanitary Napkin Attachment Means", issued to Mattingly on Aug. 26, 1986; and, U.S. Pat. No. 4,687,478, entitled "Shaped Sanitary Napkin With Flaps", issued to Van Tilburg on Aug. 18, 1987; and in Reexamination Patent B1 4,589,876 issued to Van Tilburg on Apr. 27, 1993. Some particularly preferred types of flaps are described in the following U.S. patent applications: Ser. No. 07/769,891 entitled "Absorbent Article Having Flaps and Zones of Differential Extensibility" filed in the name of Lavash, et al. on Oct. 1, 1991 (PCT Publication No. WO 93/06805, published Apr. 15, 1993); and in Ser. No. 07/906,593 entitled "Absorbent Article Having Unitary Release Material" filed in the name of Lavash, et al. and Ser. No. 07/906,629 entitled "Absorbent Article Having Tucked Flaps" filed in the name of Osborn, et al., both filed Jun. 30, 1992.

While preferred sanitary napkin embodiments of the present invention have been described, numerous other sanitary napkin embodiments are disclosed in the literature. These could also be provided with the body-conforming acquisition element of the present invention. Several such sanitary napkins are disclosed in U.S. Pat. No. 4,425,130, "Compound Sanitary Napkin" issued to DesMarais on Jan. 10, 1984; U.S. Pat. No. 4,321,924, "Bordered Disposable Absorbent Article" issued to Ahr on Mar. 30, 1982; the aforementioned U.S. Pat. No. 4,950,264 issued to Osborn on Aug. 21, 1990, U.S. Pat. No. 5,007,906 entitled "Decoupled Sanitary Napkin" issued to Osborn, et al. on Apr. 16, 1991; the aforementioned U.S. Pat. No. 5,009,653 issued to Osborn on Apr. 23, 1991; U.S. Pat. No. 4,917,697 entitled "Sanitary Napkin Having Flaps and Stress Relief Means" issued to Osborn et al. on Apr. 17, 1990; U.S. Pat. Nos. 4,988,344 and 4,988,345 entitled "Absorbent Articles With Multiple Layer Absorbent (Cores)" and "Absorbent Articles With Rapid Acquiring Absorbent Cores" issued to Reising, et al. and Reising, respectively, on Jan. 29, 1991; U.S. Pat. No. 5,171,302 entitled "Absorbent Article With Central Hinge" issued to Buell on Dec. 15, 1992; U.S. Pat. No. 5,197,959 entitled "Absorbent Article" issued to Buell on Mar. 30, 1993; and in U.S. patent application Ser. No. 07/605,583 entitled, "Sanitary Napkin Having Components Capable of Separation in Use" filed in the name of Visscher, et al. on Oct. 29, 1990 (PCT Publication No. WO 92/07535, published May 14, 1992); U.S. patent application Ser. No. 07/630,451 entitled "Sanitary Napkin Having Transversely Segmented Core" filed in the name of Osborn et al. on Dec. 19, 1990 (PCT Publication No. 92 WO/10984, published Jul. 9, 1992); and U.S. patent application Ser. No. 07/707,233 entitled "Sanitary Napkin Having Laterally Extensible Means for Attachment to the Undergarment of the Wearer", filed May 21, 1991 in the name of Osborn et al. (EPO Application No. 90202826.5), in U.S. patent application Ser. No. 07/874,872 entitled "Generally Thin, Flexible Sanitary Napkin Having Stiffened Center" filed in the name of Osborn on Apr. 28, 1992, and the aforementioned "Curved Bun" patent applications.

The sanitary napkin described herein can also be comprised one or more extensible components. In one preferred embodiment, most or all of the components are extensible to provide a degree of extensibility (on the order of 15%–40%) to the absorbent article. This extensibility may provide better in-use fit and comfort. In a particularly preferred alternative embodiment, the sanitary napkin 20 is comprised of components that are extensible (preferably, capable of stretching), particularly in the longitudinal direction when the sanitary napkin is worn. Suitable extensible absorbent articles are described in U.S. Patent Application entitled "Stretchable Absorbent Articles" filed in the name of Osborn, et al. on Jul. 23, 1992 (PCT Publication No. WO 93/01785 published Feb. 4, 1993).

The terms "panty liner" or "pantiliner" refer to absorbent articles that are less bulky than sanitary napkins which are generally worn by women between their menstrual periods. Suitable absorbent articles in the form of pantiliners which could be provided with the body-conforming acquisition element of the present invention are disclosed in U.S. Pat. No. 4,738,676 entitled "Pantiliner" issued to Osborn on Apr. 19, 1988.

The term "incontinence article" refers to pads, undergarments (pads held in place by a suspension system of same type, such as a belt, or the like), inserts for absorbent articles, capacity boosters for absorbent articles, briefs, bed pads, and the like, regardless of whether they are worn by adults or other incontinent persons. Suitable incontinence articles that can be provided with the body-conforming acquisition element described herein are disclosed in U.S. Pat. No. 4,253,461 issued to Strickland, et al. on Mar. 3, 1981; U.S. Pat. Nos. 4,597,760 and 4,597,761 issued to Buell; the above-mentioned U.S. Pat. No. 4,704,115; U.S. Pat. No. 4,909,802 issued to Ahr, et al.; U.S. Pat. No. 4,964,860 issued to Gipson, et al. on Oct. 23, 1990; and in U.S. patent application Ser. Nos. 07/637,090 and 07/637,571 filed respectively by Noel, et al. and Feist, et al. on Jan. 3, 1991 (PCT Publication No. WO 92/11830 entitled "Absorbent Article Having Rapid Acquiring, Multiple Layer Absorbent Core" published in the name of Noel, et al. and PCT Publication No. WO 92/11831 entitled "Absorbent Article Having Rapid Acquiring, Wrapped Multiple Layer Absorbent Body" published in the name of Feist, et al., both published on Jul. 23, 1992).

The focus of the present invention is on absorbent articles that are intended to be worn in the crotch region of the wearer's undergarments. However, the features of the present invention could also be used in absorbent articles such as diapers. Diapers are absorbent articles worn by infants and incontinent persons that are fastened about the waist of the wearer. Suitable diapers that can be provided with a window having an acquisition element positioned therein are disclosed in U.S. Pat. No. 3,860,003 issued to Buell on Jan. 14, 1975, and U.S. Pat. No. 5,151,092 issued to Buell, et al. on Sep. 29, 1992.

4. Method of Making the Absorbent Article.

A. In General.

The sanitary napkin of the present invention can be made in a variety of ways. The sanitary napkin 20 is assembled in the following manner. For simplicity, the assembly is described in terms of making one possible sanitary napkin embodiment (the embodiment shown in the drawings) one possible method of making the sanitary napkin by hand, and with the steps carried out in one possible order. The steps described below can be carried out in many other orders. All such alternatives are within the scope of the present invention.

The first step in the assembly is to begin to assemble the absorbent core 42. The components for the absorbent core 42 are obtained. The absorbent core 42 that will be used is the preferred laminate described above that comprises two layers of cross-linked cellulose fibers 43 and 45 with absorbent gelling material particles 41 therebetween.

The web of cross-linked cellulose fibers (or portion thereof) that will form the upper layer 43 of the core 42 is provided with a window cut out having one of the configurations described above. The window is provided in the portion of the upper layer 43 that will lie in the central region 32 of the completely assembled sanitary napkin. Adhesive is sprayed onto the side of the web of cross-linked cellulose fibers that will form the inside surface of the sheet that is folded to form the core. The absorbent gelling material particles 41 are placed on top of the adhesive on the cross-linked cellulose fibers.

The capillary channel fibers 90 are obtained. Some particularly suitable capillary channel fibers are those designated SW-337 available from the Eastman Chemical Company. The capillary channel fibers are made from polyethylene teraphthalate (PET) with an Inherent Viscosity of 0.76. The PET preferably has 0.2% $Tio_2$ added thereto. After the fibers are formed, they are preferably coated with 0.7% LK 5570 lubricant. The fibers preferably have a denier per fiber of about 24 and 6 inch staple (cut length). The capillary channel fibers preferably have an H-shaped cross-section with a channel width of 39 microns and a channel depth of 55 microns. The width and depth of the channels of suitable capillary channel fibers can vary, in different embodiments, however.

The capillary channel fibers 90 are preferably substantially curled, and more preferably helically curled. The fibers are curled at a frequency of about 6 curls per inch, and the amplitude of the curls is about 0.5 mm. The curling of the fibers, like a number of the other properties of the same, can vary in other embodiments. For instance, fibers having various different amounts of curling, as well as uncurled fibers may also be used. Uncurled fibers may be used when it is desirable to keep the bulk of the sanitary napkin at relatively low levels (such as in a portion of the sanitary napkin used primarily for distribution of liquids), but may be less preferred in portions of the sanitary napkin used for acquisition of liquids.

The SW-337 fibers are preferably formed into a continuous tow of fibers. The tow is then cut and formed into a staple sliver. The sliver of fibers preferably has a nominal total denier of about 80K (80,000). The capillary channel fibers are preferably cut to form a first 7 inch long sliver comprised of 1.2 grams of fibers (that will serve as the upper sliver 44A) a second 3 inch long sliver comprised of 0.3 grams of fibers (that will serve as the lower sliver 44B).

In alternative embodiments, smaller quantities of capillary channel fibers (e.g., as low as 0.1 gram, or lower) can be used if other types of fibers are used in the sliver with the capillary channel fibers and/or higher efficiency capillary channel fibers are used. "Higher efficiency" capillary channel fibers can be those formed with thinner walls, and, thus, reduced weight. Such constructions may be desirable since capillary channel fibers can be relatively expensive. At the other end of the spectrum, larger quantities of capillary channel fibers (e.g., up to 3 5 grams, or more) can be used, if desired.

The second sliver of capillary channel fibers is placed on top of the absorbent gelling material 41 on the portion of the cross-linked cellulose fiber web that will serve as the bottom layer 45 of the core. The second sliver is placed so that it will be oriented along the longitudinal centerline L of the completely assembled sanitary napkin. The first sliver of capillary channel fibers is placed on top of, and oriented similarly to the second sliver of fibers.

The portion of the web of cross-linked cellulose fiber that will form the upper layer 43 of the core 42 is folded into a "C" folded configuration, or more particularly, an "e" configuration so that the window is on top of the first sliver 44A of capillary channel fibers. This forms an absorbent core pre-assembly.

The secondary topsheet 46 material is provided, preferably in the form of a Ft. Howard airlaid tissue layer. The layer of material comprising the secondary topsheet 46 is also provided with a window cut out. The secondary topsheet 46 is placed on the body-facing side of the absorbent core pre-assembly. The nonwoven layer 48 is positioned on the garment-facing side of the core pre-assembly. This forms the absorbent core/nonwoven sheet laminate or "sandwich" 51. The components of the absorbent core/nonwoven sheet laminate 51 are then stitched together along stitching lines 70 such as those shown in FIG. 6.

The absorbent core/nonwoven sheet laminate 51 and the other components of the sanitary napkin are then assembled. The backsheet 40 material is first placed on a surface. The two strips of construction adhesive 68 are placed on the backsheet 40 near the longitudinal side edges of the backsheet material. The absorbent core/nonwoven sheet laminate 51 is then placed on top of the construction adhesive 68 to secure it to the backsheet 40 material.

The topsheet 38 is sprayed with the topsheet bonding adhesive 66 on its garment-facing side 38B. Preferably, the adhesive 66 is applied in a spiral pattern. The topsheet 38 is then placed on top of and secured to the absorbent core/nonwoven sheet laminate 51 by the topsheet bonding adhesive to form a pre-assembled sanitary napkin.

The sanitary napkin is then sealed around its perimeter 26. In the preferred process described herein, the perimeter seal 64 is formed by a heated element. The heated element can be any suitable type of heating device, such as a heated plate, a bar sealer, a spatula type sealer, etc. The subsequent steps of the assembly of the sanitary napkin, such as cutting any excess material outboard of the perimeter seal can be performed in any suitable manner.

In addition to the method described above, the sanitary napkin can be made in a curved configuration. Suitable methods for making a sanitary napkin in a curved configuration are described in the aforementioned U.S. patent application Ser. No. 07/915,134 filed in the name of Hines, et al. (PCT Publication No. WO 93/01784.) Further, any or all of the steps of assembling the sanitary napkin could be performed by machine. Suitable methods for assembling the components of the sanitary napkin by machine are described in the aforementioned PCT patent application published in the name of Hines, et al. In other embodiments, some of the techniques described in P&G U.K. Patent Application 2 168 253A published in the name of Baird, et al. on Jun. 16, 1986 and in U.S. patent application Ser. No. 07/882,738 filed in the name of Taylor, et al. on May 14, 1992 could be used in the construction of the sanitary napkin.

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

5. Test Methods.

The following are the procedures for determining whether the sanitary napkin (or other absorbent article) falls within the scope of those appended claims that require measurement of certain properties of the article.

All measurements are made on newly unpacked, and unless otherwise stated, dry (i.e., not wetted or soiled) absorbent articles. The articles should be removed from their package for at least 30 minutes and handled carefully to avoid compressing, or otherwise affecting the properties of the same. Unless otherwise stated, all tests are performed on samples that have been conditioned by leaving them in a room at 50% relative humidity and at 73° F. for a period of two hours prior to the tests.

A. Determination of Whether a Hump is Formed by Acquisition Component.

The sample can be tested in two alternative ways to determine whether a hump is formed when an acquisition component is in its compressed configuration. If the sample forms a hump when either procedure is followed, the absorbent article will be considered to fall within the scope of the appended claims which require the presence of a hump.

(1) Visual Observation During Wear.

The absorbent article is worn and examined when the wearer is standing and the wearer's thighs are brought together as close as possible. This places the absorbent article (and any acquisition component therein) in a compressed configuration. The configuration of the absorbent article and the acquisition component in their compressed configuration can be recorded such as by photographing the absorbent article, or by any other suitable means that accurately preserves the absorbent article and the acquisition component in their compressed configurations.

Other suitable methods for recording the compressed configuration of an absorbent article are described in U.S. Pat. No. 5,197,959 issued to Buell on Mar. 30, 1993. Such methods include Magnetic Resonance Imaging (MRI) and preparing casts of the product in its compressed configuration. Magnetic resonance images of women wearing sanitary napkins which have been saturated with mineral oil can give a depiction of the shape a wet sanitary napkin has when worn.

Cast molding can be used for the purpose of permanently "freezing" the absorbent article in a compressed configuration so that the article can be further studied. The cast mold can be made from a number of different materials. The material that is used may penetrate into the absorbent means. Two materials that have been found suitable are a hard casting material which is marketed as EnviroTex 1 to 1 Polymer Coating by Environmental Technology, Inc. of Fields Landing, Calif., and a soft casting material which is a mixture of 46% Veisamid 125 resin which is marketed by the Henkel Corporation of Minneapolis, Minn., 31% EPON 812 hardener which is marketed by Polaron Equipment Limited of Watford, Conn. and 23% 1,1,1 Trichloroethane thinner. The casting material can be poured directly into the absorbent article if the "in use" configuration is susceptible to such (i.e., for example, boat or cupped shaped). If not, a thin sheet of aluminum foil can be placed around and under the napkin so as to create a receiver for the mixture. The aluminum foil receiver can then be filled so as to submerge the napkin in the casting material. After the casting material has set, any number of lateral cross-sections can be cut along the longitudinal length of the absorbent article. From these lateral cross-sections, a person can determine whether a hump having the specified properties has been formed.

(2) Laboratory Procedure (The "Lateral Compression" Test).

Figure 9:
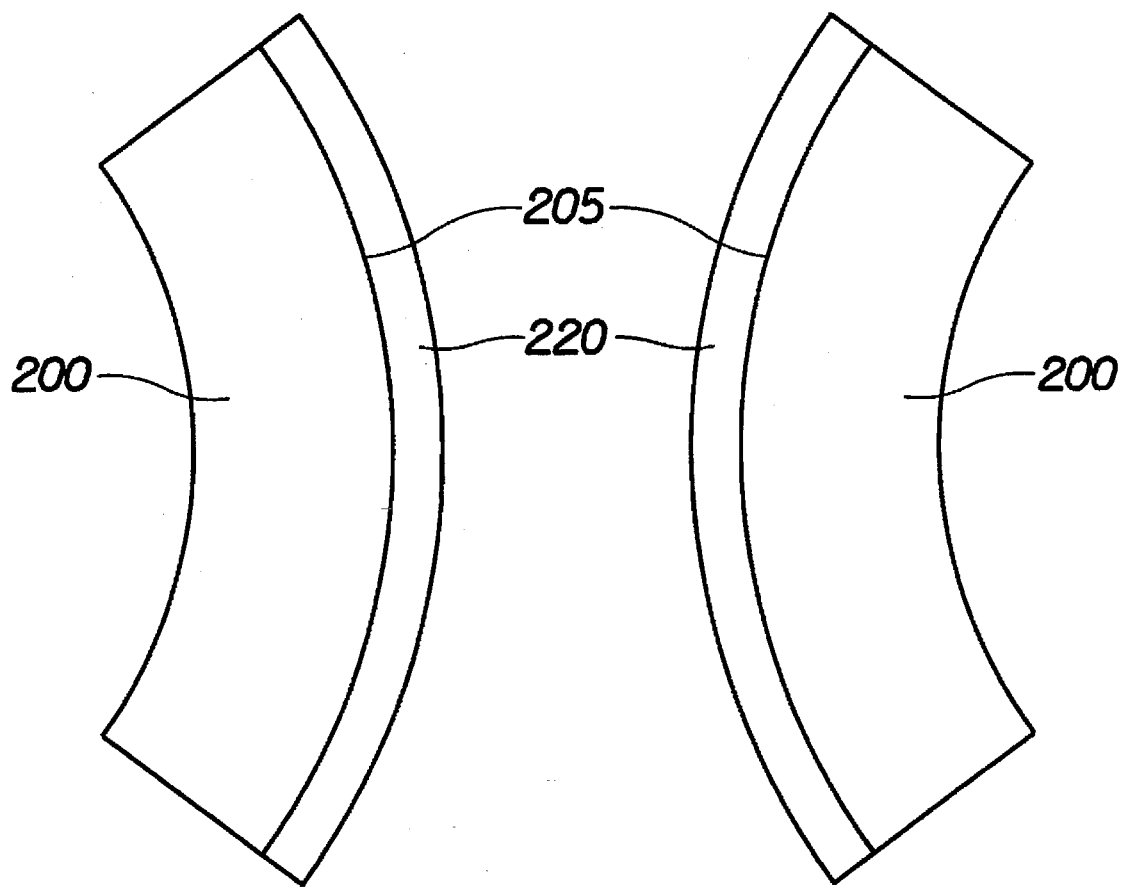
FIG. 9 is a top plan view of the test apparatus plungers.

This test involves the use of a test apparatus shown in FIG. 9. The apparatus comprises a pair of jaws (plungers) 200, a supporting surface for the absorbent article to be tested, and a force supplying mechanism for each plunger. The plungers have curved faces 205 having a radius of about 76.2 millimeters. The curvature of the plungers 200 is intended to approximate the curvature of the thighs of a representative number of women. The plungers 200 have a face height of about 51.0 millimeters, and a bottom lip 220 having a width of about 5.0 millimeters and a thickness of about 5.0 millimeters.

In the test, the absorbent article is centered on the supporting surface between the plungers with the body surface of the absorbent article facing upward. The transverse centerline of the absorbent article and any acquisition component therein should be aligned with the midpoints of the faces of the plungers. If the two differ, separate measurements should be taken. Any fastener, such as any panty fastening adhesive, as well as any covering thereon should be removed. If the fastener cannot be removed, it should be covered with a material that does not interfere with the lateral compressibility of the absorbent article. The plungers are set to start at a width slightly greater than that of the absorbent article (e.g., a width of about 2 to about 3 inches (about 5 cm to about 7.6 cm), and to compress the absorbent article to a width of one inch (2.5 cm). The force should be applied steadily. The force should be applied at such a rate that the absorbent article is compressed from its initial width to a one inch width in about 30 seconds.

The size of the hump at its maximum amplitude during the compression should be measured. This can be done by providing the test apparatus with a calibrated vertical rod that can be raised and lowered from directly above the hump. One measurement of the caliper of the absorbent article is taken before the article is compressed. This first measurement is taken in the area where the point of maximum amplitude of the hump will be formed. The rod is raised when the hump is compressed. A second measurement is taken by lowering the rod over the point of maximum amplitude of the hump after the absorbent article has been compressed. The difference between the two measurements is the height of the hump.

B. Measurement of Size of the Hump Formed by Acquisition Component.

The size (that is, the height) of the hump formed when the acquisition component is in its compressed configuration is measured by physically measuring the hump formed under either Test Procedure A(1) or Test Procedure A(2) above.

The height of the hump, especially for performing the measurement in Test Procedure A(1), is the perpendicular distance from the point of maximum amplitude of the hump, A, to the base of the hump. The measurement of the height of the hump is described with reference to FIGS. 4 and 4A. The base of the hump is designated by reference letter B. The base of the hump is determined by first locating the inflection points, I, where the hump causes a discontinuity in the curvature of the body surface of the absorbent article. An imaginary line, B, is drawn which connects the inflection points.

C. Compressibility of Acquisition Component.

The compressibility of the acquisition component in the absorbent article is measured according to the following Compression Caliper Test. The Compression Caliper Test is a version of the caliper test set out in U.S. Pat. No. 5,009,653 issued to Osborn. In the Compression Caliper test, however, two caliper measurements are taken, an original caliper, and a compressed caliper.

A comparator gauge, and specifically the Ames, Model 130 with dial indicator Model 482, available from the B. C. Ames, Company of Waltham, Massachusetts is needed. The comparator gauge should typically have a circular comparator foot made of aluminum and a weight of 10.0 grams and a contact surface of 5.16 square centimeters. The gauge is provided with an 80.0 gram stainless steel weight to provide a total of 0.25 psi pressure. If due to the plan view shape of the region to be tested, it is not possible to use a circular comparator foot and achieve an accurate measurement of the region, a 1"×¼" rectangular comparator foot should be used and a test weight should be used that provides a total pressure of 0.25 psi. The comparator gauge is zeroed. The weight is placed on the spindle extending above the comparator dial. Any adhesive release paper is removed from the absorbent article and the adhesive is sprinkled with corn starch. The comparator foot is raised, and the absorbent article is placed garment surface down on the base plate. The absorbent article is positioned on the base plate so that when the foot is lowered it is in the region of the absorbent article for which the measurement is desired. Try to smooth out or avoid any wrinkles in the absorbent article. Gently lower the foot onto the absorbent article. Determine the caliper of the absorbent article by reading the comparator dial 30 seconds after the foot comes in contact with the absorbent article.

The "original caliper" is measured under a 10 gram comparator foot with no test weight. An 80 gram test weight is then placed on the sample with the 10 gram comparator foot, and the caliper is measured. This latter measurement is the "compressed caliper".

$$\text{The Percentage of Original Caliper} = \frac{\text{compressed caliper}}{\text{original caliper}} \times 100\%$$

The Caliper Recovery Test is also a modified version of the caliper test set out in U.S. Pat. No. 5,009,653 issued to Osborn. The "original caliper" is measured under a 10 gram comparator foot with no weight. An 80 gram test weight is then placed on the sample with the 10 gram comparator foot for 5 seconds. The 80 gram test weight is then taken off, and the caliper of the sample is again measured after 30 seconds under the 10 gram comparator foot. This latter caliper measurement is the "recovered caliper".

$$\text{Recovery (\%)} = \frac{\text{recovered caliper}}{\text{original caliper}} \times 100\%$$

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article for wearing in a crotch region of a wearer's undergarment, said absorbent article having a body surface, a garment surface, a longitudinal centerline, and a transverse centerline, said absorbent article comprising:

a liquid pervious topsheet;

a liquid impervious backsheet joined to said topsheet;

an absorbent core positioned between said topsheet and said backsheet, said absorbent core comprising a first layer and a second layer wherein said second layer underlies said first layer; and an acquisition component positioned such that at least a portion of said acquisition component is disposed above at least a portion of said absorbent core and at least a portion of said acquisition component is disposed between said first layer and said second layer of said absorbent core, said acquisition component being in liquid communication with said absorbent core and comprising a mass of wet and dry resilient material, said acquisition component having a compressed configuration when it is subjected to inward compressive forces in the direction of and along said transverse centerline and an uncompressed configuration when said compressive forces are absent, wherein when said acquisition component is in its uncompressed configuration, the body surface of said absorbent article overlying said acquisition component forms a continuous curve having a curvature, and when said acquisition component is in its compressed configuration, said acquisition component forms a hump on said body surface.

2. The absorbent article of claim 1 wherein said hump has a height of at least about 3 mm.

3. The absorbent article of claim 2 wherein said hump has a height of less than or equal to about 15 mm.

4. The absorbent article of claim 2 herein said hump has a length of between about 4 cm to about 10 cm.

5. The absorbent article of claim 4 wherein said hump has a base with a width of between about 1 cm and about 5 cm.

6. The absorbent article of claim 1 wherein said hump is sized to at least partially fit in the space between the wearer's labia majora.

7. The absorbent article of claim 1 wherein said hump is wedge-shaped.

8. The absorbent article of claim 1 wherein said hump is cusp-shaped.

9. The absorbent article of claim 8 wherein said hump has a pair of curved sides each having a first radius of curvature, and an upper portion comprising a point of maximum amplitude of said hump, and said upper portion of said hump has a second radius of curvature that is less than said first radius of curvature.

10. The absorbent article of claim 1 wherein said acquisition component is self-draining.

11. The absorbent article of claim 1 wherein said acquisition component comprises a fibrous component.

12. The absorbent article of claim 11 wherein the longitudinal centerline extends in a longitudinal direction, and said acquisition component is comprised of fibers that preferentially distribute liquids in the longitudinal direction.

13. An absorbent article for wearing in a crotch region of a wearer's undergarment, said absorbent article having a body surface, a garment surface, and a transverse centerline, said absorbent article comprising:

a liquid pervious topsheet;

a liquid impervious backsheet joined to said topsheet;

an absorbent core positioned between said topsheet and backsheet, said absorbent core comprising a first layer and a second layer wherein said second layer underlies said first layer; and an acquisition component positioned such that at least a portion of said acquisition component is disposed above at least a portion of said absorbent core and at least a portion of said acquisition component is disposed between said first layer and said second layer of said absorbent core, said acquisition component comprising a wet and dry resilient material, said acquisition component having a compressed configuration when it is subjected to inward compressive forces along said transverse centerline and an uncompressed configuration when such forces are absent, wherein when said acquisition component is in its compressed configuration, said acquisition component forms a hump on the body surface; wherein said absorbent core has a window cut out therein and at least a portion of said acquisition component is positioned within said window.

14. The absorbent article of claim 13 wherein said topsheet has a window cut out therein.

15. The absorbent article of claim 14 wherein the window cut out in said topsheet is the same size as the window cut out in said absorbent core.

16. The absorbent article of claim 14 wherein the window cut out in said topsheet is smaller than the window cut out in said absorbent core.

17. The absorbent article of claim 14 wherein the window cut out in said topsheet is larger than the window cut out in said absorbent core.

18. The absorbent article of claim 13 wherein only said absorbent core has a window cut out therein.

19. The absorbent article of claims 13 or 18 further comprising a wicking layer positioned between said absorbent core and said backsheet.

20. The absorbent article of claim 19 wherein said wicking layer is positioned between said topsheet and said absorbent core.

21. An absorbent article for wearing in a crotch region of a wearer's undergarment, said absorbent article having a body surface, a garment surface, a longitudinal centerline, a transverse centerline, two longitudinal side edges, and two transverse end edges, said absorbent article comprising:

a liquid pervious topsheet;

a liquid impervious backsheet joined to said topsheet;

an absorbent core positioned between said topsheet and backsheet, said absorbent core having a first layer facing said topsheet, a second layer facing said backsheet wherein said first layer has a window cut out therein;

an acquisition/distribution component, at least a part of said acquisition/distribution component being positioned within said window and at least a portion of said acquisition/distribution component being positioned between said first layer and said second layer, said acquisition/distribution component having a compressed configuration wherein said acquisition/distribution component forms a hump on the body surface that protrudes from said window when said acquisition/distribution component is subjected to inward compressive forces along said transverse centerline and uncompressed configuration when such forces are absent wherein said acquisition/distribution component lies relatively flat; and a fastener on the garment surface of said absorbent article for fastening said absorbent article to said undergarment.

22. The absorbent article of claim 21 wherein said window is centered along said longitudinal centerline.

23. The absorbent article of claim 22 having a length, a width, a first end region, a second end region, and a central region disposed between said end regions, wherein said end regions each extend from each transverse end edge about ⅛ to ⅓ of the length of the absorbent article toward said transverse centerline and said window is in said central region.

24. The absorbent article of claim 23 wherein the window in said upper portion of said absorbent core has a length and a width, and the length of said window is between about 4 cm and about 10 cm, and the width of said window is between about 1 cm and about 5 cm.

25. The absorbent article of claim 24 wherein the length of said window is about 5 cm and the width of said window is about 2.5 cm.

26. The absorbent article of claim 21 wherein said absorbent core comprises at least one layer of absorbent gelling material and said upper and lower portions of said core each comprise a layer of cross-linked cellulose fibers.

27. The absorbent article of claim 21 wherein said acquisition/distribution component comprises a resilient material.

28. The absorbent article of claim 27 wherein said acquisition/distribution component comprises capillary channel fibers having intra-fiber capillary channels.

29. The absorbent article of claims 21 or 28 wherein said acquisition/distribution component comprises a batt of fibers.

30. The absorbent article of claim 28 wherein said capillary channel fibers are in the form of a staple sliver.

31. The absorbent article of claim 28 wherein said capillary channel fibers are in the form of tow.

32. The absorbent article of claim 21 wherein said acquisition/distribution component comprises a nonwoven web.

33. An absorbent article for wearing in a crotch region of a wearer's undergarment, said absorbent article having a body surface, a garment surface, a longitudinal centerline, and a transverse centerline, said absorbent article comprising:

a liquid pervious topsheet;

a liquid impervious backsheet joined to said top sheet;

an absorbent core positioned between said topsheet and said backsheet, said absorbent core comprising a first layer and a second layer wherein said second layer underlies said first layer, and said first layer of said absorbent core having a window cut out therein; and a resilient acquisition component positioned within said window such that at least a portion of said acquisition component is dispose between said first layer and said second layer of said absorbent core, said acquisition component comprising capillary channel fibers having intra-fiber capillary channels, said acquisition component being in liquid communication with said absorbent core.

* * * * *